· US009340831B2

United States Patent
Dai et al.

(10) Patent No.: US 9,340,831 B2
(45) Date of Patent: May 17, 2016

(54) GEL-TETHERED MOLECULAR BEACONS

(71) Applicants: Rutgers, The State University of New Jersey, New Brunswick, NJ (US); Stevens Institute of Technology, Hoboken, NJ (US)

(72) Inventors: Xiaoguang Dai, North Bergen, NJ (US); Salvatore A. E. Marras, Roselle Park, NJ (US); Matthew Libera, New Providence, NJ (US)

(73) Assignees: Rutgers, the State of New Jersey, New Brunswick, NJ (US); Stevens Institute of Technology, Hoboken, NJ (US)

( * ) Notice: Subject to any disclaimer, the term of this patent is extended or adjusted under 35 U.S.C. 154(b) by 0 days.

(21) Appl. No.: 14/348,197

(22) PCT Filed: Sep. 28, 2012

(86) PCT No.: PCT/US2012/057888
§ 371 (c)(1),
(2) Date: Mar. 28, 2014

(87) PCT Pub. No.: WO2013/089888
PCT Pub. Date: Jun. 20, 2013

(65) Prior Publication Data
US 2014/0329713 A1    Nov. 6, 2014

Related U.S. Application Data

(60) Provisional application No. 61/581,460, filed on Dec. 29, 2011, provisional application No. 61/541,475, filed on Sep. 30, 2011.

(51) Int. Cl.
*C12Q 1/68*    (2006.01)

(52) U.S. Cl.
CPC ............ *C12Q 1/6837* (2013.01); *C12Q 1/6834* (2013.01); *C12Q 1/6876* (2013.01)

(58) Field of Classification Search
CPC ........................... C12Q 1/6837; C12Q 1/3883
USPC ................................................. 435/6.1, 287.2
See application file for complete search history.

(56) References Cited

U.S. PATENT DOCUMENTS

| 2005/0008828 A1 | 1/2005 | Libera et al. |
| 2005/0196760 A1* | 9/2005 | Pemov et al. ..................... 435/6 |
| 2006/0014003 A1 | 1/2006 | Libera et al. |
| 2009/0087835 A1 | 4/2009 | Miller et al. |

(Continued)

OTHER PUBLICATIONS

Wang et al "Label-free hybridization detection fo a single nucleotide mismatch by immobilization of molecular beacons on an agarose film", Nucleic Acid Research, 2002, vol. 30, No. 12 e61, pp. 1-9.*

(Continued)

*Primary Examiner* — Betty Forman
(74) *Attorney, Agent, or Firm* — Fox Rothschild LLP; Gerard P. Norton; Michael S. Montgomery

(57) ABSTRACT

The present invention relates to surface-patterned microgels to which molecular beacon probes are immobilized. The immobilized molecular beacon probes exhibit both low non-specific background and high specific fluorescence. Also disclosed are related arrays, related detection methods, and preparation methods.

17 Claims, 7 Drawing Sheets

(56) References Cited

U.S. PATENT DOCUMENTS

2009/0209436 A1* 8/2009 Larman et al. .................. 506/9
2010/0204461 A1   8/2010 Beadling et al.

OTHER PUBLICATIONS

Tan et al., "Moecular Beacons: A Novel DNA Probe for Nucelic Acid and Protein Studies," Chemistry (2000) 6(7):1107-111.

Extended Eurpean Search Report issued in Application No. 12857357.3 dated Apr. 30, 2015.

Dai et al., "Dip-pen microarraying of molecular beacon probes on microgel thin-film substrates," The Analyst, vol. 139, No. 21, Sep. 1, 2014, pp. 5568-5575.

Dai et al., "Surface-patterned microgel-tethered molecular beacons," Soft Matter, vol. 8, No. 11, Jan. 1, 2012, p. 3067.

Krsko et al., "Biointeractive hydrogels," Materials Today, vol. 8, No. 12, Dec. 1, 2005, pp. 36-44.

Krsko et al., "E-beam-patterned hydrogels to control nanoscale surface bioactivity," Proceedings of SPIE—The International Society for Optical Engineering—Nanofabrication: Technologies, Devices, and Applications II 2005 SPIE US, vol. 6002, 2005.

Ramachandran et al., "Target discrimination by surface-immobilized molecular beacons designed to detect Francisella tularensis," Biosensors and Bioelectronics, vol. 19, No. 7, Feb. 15, 2004, pp. 727-736.

Wang et al., "Label-free hybridization detection of a single nucleotide mismatch by immobilization of molecular beacons on a agarose film," Nucleic Acids Research, vol. 30, No. 12, Jun. 15, 2002, pp. E61-1.

* cited by examiner

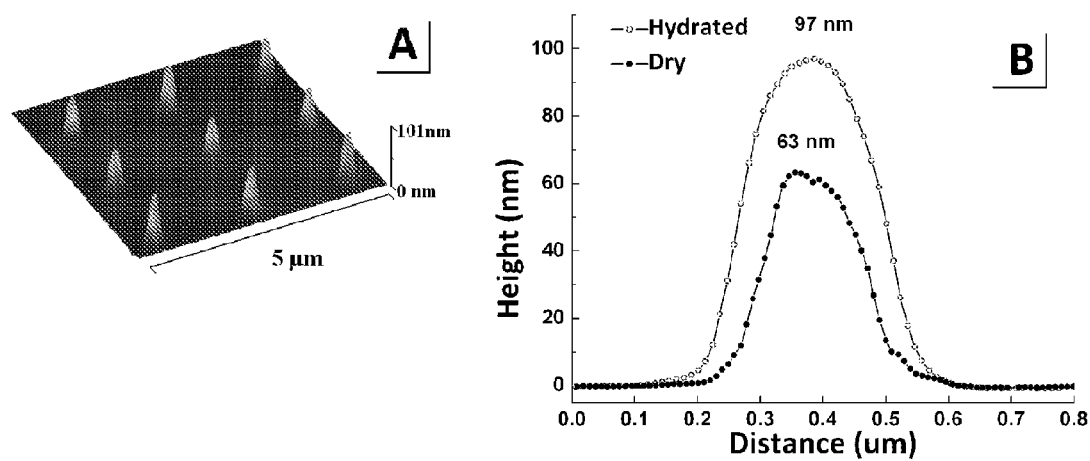
FIG. 1A and B
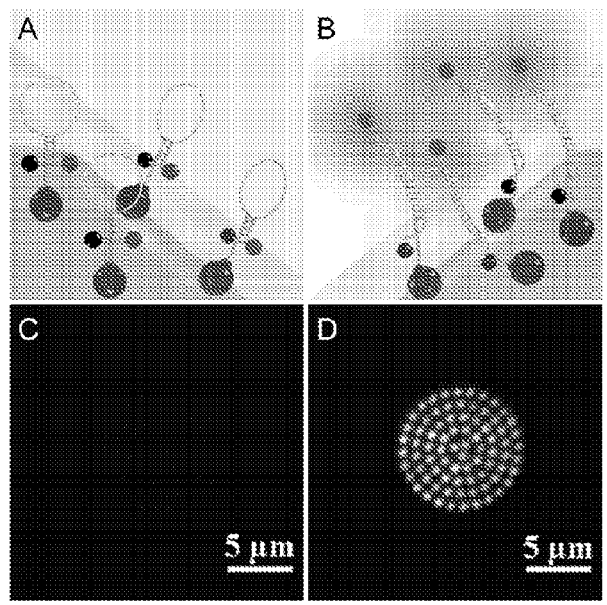
FIG. 2A-D

FIG. 4A-C

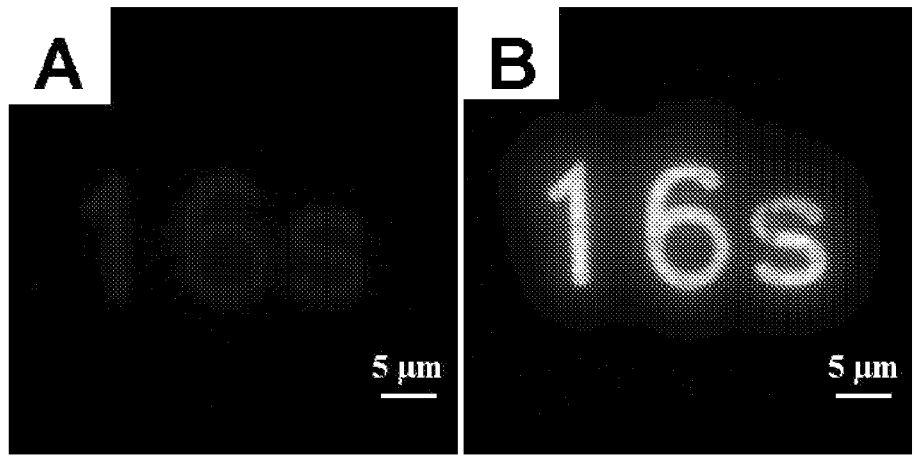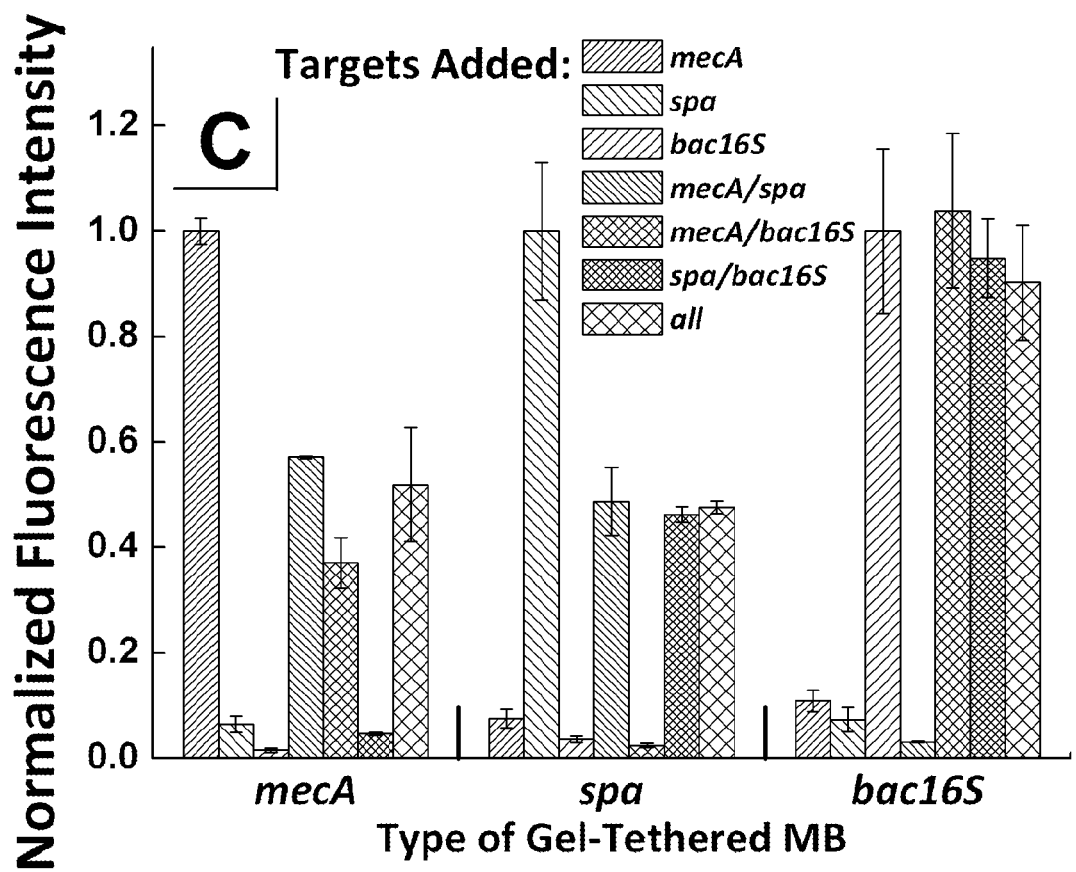
FIG. 6A-C

US 9,340,831 B2

GEL-TETHERED MOLECULAR BEACONS

CROSS-REFERENCE TO RELATED APPLICATIONS

This application is a U.S. National Phase of International Application No. PCT/US2012/057888, filed on Sep. 28, 2012, which claims the priority of U.S. Provisional Application No. 61/581,460 filed on Dec. 29, 2011 and U.S. Provisional Application No. 61/541,475 filed on Sep. 30, 2011. The content of all applications are incorporated herein by reference in their entirety.

GOVERNMENT INTERESTS

The invention disclosed herein was made, at least in part, with Government support under Grant No. W911NF-07-0543 from the U.S. Army Research Office and Grant No. RO1 MH-079197 from the National Institutes of Health. Accordingly, the U.S. Government has certain rights in this invention.

FIELD OF THE INVENTION

This invention relates to gel-tethered molecular beacon probes, related microarrays, and related analysis and detection uses.

BACKGROUND OF THE INVENTION

DNA/RNA microarrays have become a leading method in gene analysis, medical diagnosis and disease prevention, in large measure due to the significant automation and high throughput they bring. Based on the hybridization between surface-immobilized probes and DNA/RNA targets, large amounts of genetic information can be extracted from one assay very efficiently. Many such assays use fluorescence-based detection techniques that typically require multiple steps to incorporate fluorophores into target sequences. An attractive alternative is to use a platform containing probes that become fluorescent upon binding to their target.

Molecular beacon probes are one such category of self-reporting probe (Tyagi et al. *Nat. Biotechnol.*, 1996, 14, 303-308 and Tyagi et al. *Nat. Biotechnol.*, 1998, 16, 49-53). However, the probes' signal-to-background ratio is often significantly reduced when molecular beacon probes are immobilized on solid substrates as needed in a microarray format. Several approaches have been used to decrease the background fluorescence and increase the hybridization of immobilized molecular beacon probes. Despite these efforts, the differences between molecular beacon probes immobilized on solid substrates and those in solution remain poorly understood. There is a need for surface-immobilized molecular beacon probes with high SBR ratios.

SUMMARY OF INVENTION

This invention relates to gel-tethered molecular beacon probes, related microarrays, and related analysis and detection uses in detecting multiple biological targets.

In one aspect, the invention provides a device for detecting multiple biological targets (e.g., nucleic acids or peptides). The device includes a plurality of quenched probes capable of binding to the multiple targets, and an array of spatially separated structures on a solid surface.

In the device, each structure contains a member selected from the group consisting of aqueous gels, aqueous microgels, aqueous gel coatings and aqueous gel-like coatings having chemically or physically incorporated therein a linking moiety. The structure can be a surface-patterned microgel, e.g., an electron-beam surfaced patterned microgel. The microgel can be poly(ethylene glycol) or other polymers as disclosed herein. In one example, the structure can be a biotinylated, e-beam patterned poly(ethylene glycol) microgel.

In addition, each structure has tethered thereto through the aforementioned linking moiety (e.g., a streptavidin-biotin interaction or the like) a quenched probe capable of binding to one of the targets. Each probe is a labeled single-stranded hairpin molecule that undergoes a conformational change when it binds to its target, leading to a detectable signal. The probes can be hairpin oligonucleotides labeled with a fluorophore and a non-fluorescent quencher. The oligonucleotides can include non-natural nucleotides, nucleotide analogs, or non-natural inter-nucleotide linkages. The structure is hydrophilic and interacts not more than weakly with the probes, the targets or probe-tethering molecules, thereby not interfering with construction or use of the device. Also, when hydrated in an aqueous medium, the device includes a transition region from the aqueous medium to the pure hydrated structure in which the structure becomes gradually more crosslinked. Preferably, the transition region has a thickness at least equal to the combined lengths of the probe and linking moiety. The probes, if in a solution, have a signal-to-background ratio that is not more than five times as large as they have in the device. In one embodiment, a majority of the probes are separated from the solid surface by a distance at least as large as the combined length of the probe and the linking moiety.

In a second aspect, the invention provides a conjugate for detecting a target. The conjugate has (i) a gel having a surface and (ii) a molecular beacon probe that is linked to the surface of the gel. The molecular beacon probe is specific for the target. The linkage can be a chemical bonding (or covalent link, such as disulfide bonds) or a non-covalent linkage. In one embodiment, the molecular beacon probe is linked to the gel via an affinity pair, e.g., a biotin-streptavidin pair or antibody-antigen/hapten pair. The members of each pair can be in a pair format (e.g., biotin-streptavidin) or in a sandwich format (e.g., biotin-streptavidin-biotin) as shown below. For example, the molecular beacon probe can be linked to a biotin and the surface to a biotin or streptavidin so that probe and surface can be linked via the biotin-streptavidin pair. In another embodiment, the probe could be linked to the gel by a covalent pathway provided that the chemistry of the linking is orthogonal to other functional groups on the conjugate and on the probe.

The molecular beacon probe can include one or more non-natural nucleotides, nucleotide analogs, or non-natural internucleotide linkages. The surface can be linked with a plurality of the molecular beacon probe. The gel can contain poly(ethylene glycol), poly(ethylene oxide), or other water-soluble polymers including: poly(acids) such as poly(acrylic acid) or poly(methacrylic acid); poly(N-isoacrylimide), and poly(vinyl pyrrolidone); as well as co-polymers of these and other polymer moieties. The gel can be a microgel. In one example, the microgel is linked with 7,000 or more (e.g., 8,000, 9,000, 10,000, 11,000, 12,000, or 15,000) of the molecular beacon probe. In some embodiments, the microgel is 100-10,000 nm in diameter, e.g., 100-1,000 nm in diameter. In others, where the microgel is bound to a solid substrate, the microgel can be 40-120 (e.g., 60-100) nm in height.

The conjugate can be used for detecting various targets such as a target nucleic acid sequence or a target peptide. As disclosed herein, the gel can be hydrated so that the local environment where the molecular beacon encounters its target is as water-like as possible. As a result, the signal-to-background (SBR) ratio of the molecular beacon probe for the target can be 5 or greater, e.g., as high as 10, 20, 30 or greater. In that case, the SBR ratio can be 20% or greater of a reference SBR ratio of a reference probe identical to the molecular beacon probe, except that the reference probe is in a solution and not linked to a gel.

In one embodiment, the conjugate described above can further contain a substrate to which the gel is attached. In that case, when hydrated in an aqueous medium, the conjugate includes a transition region from the aqueous medium to a pure hydrated region within the conjugate in which the conjugate becomes gradually more crosslinked. Preferably, the transition region has a thickness at least equal to the combined length of the probe and affinity pair.

The invention also provides an array containing (i) a support having a plurality of unique locations and (ii) a plurality of conjugates of described above for different targets, where each conjugate is immobilized to a unique location of the support corresponding to a target. The conjugates can be surface-patterned on the unique locations of the surface. The probe density of at least one of the plurality of unique locations can be 5,000 or more probe/$\mu m^2$, more preferably 10,000 or more probe/$\mu m^2$, and most preferably 20,000 or more probe/$\mu m^2$. The array of this invention differs from arrays of conventional approaches at least in that conventional arrays involve only two dimensions while surface-patterned microgels on the array of this invention are three-dimensional structures. With a height of about, e.g., 50-500 nm, each microgel on a unique location can have much higher density of probe molecules projected onto the two-dimension surface of the substrate/support as compared to conventional approaches that tether probes to the substrate by spacer molecules and/or tethering moieties that are short (about the same size as the probe molecule itself). As shown in the examples below, a microgel of 400 nm in diameter and 100 nm in height had about 11,800 probes per microgel, which is equivalent to a density over 20,000 probes per sq micron ($\mu m^2$) when referenced to the area of the substrate/support.

The device, one or more conjugates, or an array described above can be used in a method for detecting the presence of one or more targets in a biological sample. The method includes (a) providing a device, one or more conjugates, or an array described above; (b) contacting the device, the one or more conjugates, or the array with the biological sample for a period of time under conditions permitting binding between the one or more targets and the corresponding molecular beacon/hairpin probes; and (c) determining the presence of the binding between the one or more targets and the corresponding probes thereby detecting the presence of the one or more targets. Because of the small size of the conjugate and the high density of the probes, the method can be carried out for high-throughput detection of multiple targets in a sample simultaneously.

The invention also provides a method for making a conjugate described above. The method includes (i) providing a gel that contains a first member of an affinity pair; (ii) contacting the gel with molecular beacon probes specific for a target, each molecular beacon probe comprising a second member of the affinity pair, for a period of time under conditions permitting binding between the first member and second member; and (iii) removing molecular beacon probes that do not bind to the first member. The providing step can be carried out by a process having the steps of obtaining a substrate; depositing on the substrate a layer of a precursor of the gel; and exposing the substrate and the layer of precursor to an electron radiation for a period of time under conditions permitting cross-linking within the gel precursor and cross-linking between the resulting gel and substrate.

Finally, the invention provides a method for making an array. The method include obtaining a plurality of conjugates described above, which are specific for a plurality of targets, respectively; obtaining a support that has a plurality of unique locations; depositing said plurality of conjugates on the plurality of unique locations, respectively.

The details of one or more embodiments of the invention are set forth in the description below. Other features, objects, and advantages of the invention will be apparent from the description and from the claims.

BRIEF DESCRIPTION OF THE DRAWINGS

FIGS. 1A and B are a set of diagram showing (A) AFM image of surface-patterned microgels formed by focused-electron-beam crosslinking of a biotinylated poly(ethylene glycol) thin film on a silanized silicon substrate; (B) line profile of microgel height in the dry and hydrated states.

FIGS. 2A-D are a set of schematic illustrations and photographs showing that, when no complementary targets are present (A), the molecular beacon assumes a hairpin conformation with its fluorophore in close proximity to its quencher, so no fluorescence is emitted. Hybridization of a molecular beacon probe to its complementary target (B) results in a conformational change of the molecular beacon, restoring fluorescence. Fluorescence images of a PEG microgel array functionalized with mecA molecular beacons before (C) and after (D) hybridization to its complementary oligonucleotide target.

FIGS. 6A-C are a set of photographs showing fluorescence microscope images (top panel) of bac16S molecular beacon probes coupled to e-beam patterned microgels: (A) exposed to mecA and spa targets; (B) exposed to mecA, spa, and bac16S targets; and a histogram (C) illustrates the high degree of specificity of each molecular beacon probe for its particular oligonucleotide target when incubated with solutions containing one, two, or three different targets.

DETAILED DESCRIPTION OF THE INVENTION

Figure 3:
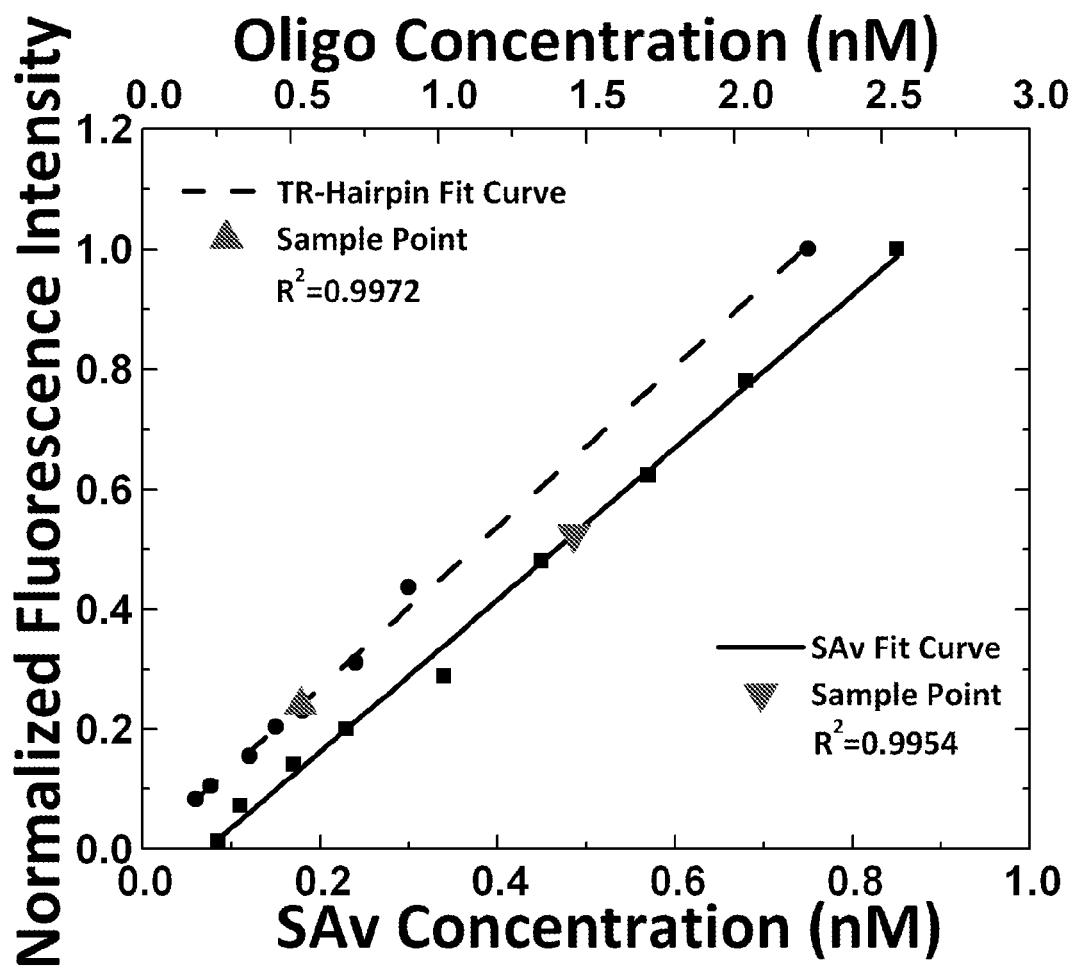
FIG. 3 is a plot showing the number of streptavidins (10, 700) and oligonucleotides (11,800) bound to a single microgel were determined by dissociating the biotin-streptavidin bond to release either Texas-red labeled streptavidins or Texas-red labeled mecA hairpin oligonucleotides from a substrate with $1.37 \times 10^7$ microgels and comparing the fluorescence intensity to a calibration curve.

This invention is based, at least in part, on an unexpected discovery that the signal-to-background ratio of surface-bound molecular beacons can be enhanced if the local environment where the molecular beacon encounters its nucleic acid target is as water-like as possible. The invention therefore addresses the unmet need for surface-immobilized molecular beacon probes with high SBR ratios and allows one to use such surface-immobilized molecular beacon probes in analyzing multiple targets simultaneously.

Indeed, as disclosed herein, the surface-bound molecular beacons of this invention can be used in connection with both synthetic oligonucleotide targets and targets derived by asymmetric PCR amplification of DNA isolated from bacterial lysates. As shown in the examples below, the signal-to-background ratios of microgel-tethered molecular beacons exceed 40, which is only a factor two to three lower than similar but untethered molecular beacon probes in solution.

Molecular Beacon Probes

Molecular beacon probes (sometimes referred to as "molecular beacons" or even "beacons") are single-stranded fluorescent nucleic acid hybridization probes, which adopt a loop and stem structure when not hybridized to a target nucleic acid (Tyagi et al. *Nat. Biotechnol.*, 1996, 14, 303-308 and Tyagi et al. *Nat. Biotechnol.*, 1998, 16, 49-53). The loop portion contains the probe sequence, complementary to the target nucleic acid sequence, and the stem structure consists of two arm sequences, which complement each other. One arm sequence contains a terminal fluorophore moiety, and the other arm sequence contains a terminal quencher moiety. The stem structure places the fluorophore and quencher moieties in close proximity, and contact-mediated energy transfer between the fluorophore and quencher quenches the fluorescent emission of the fluorophore. In the presence of a target nucleic acid, a stable and rigid, double-stranded hybrid is formed between the probe and target sequence, forcing the stem structure to unfold and thus separating the fluorophore and quencher to restore fluorescence.

As mentioned above, molecular beacons are self-reporting probes that have proved to be extremely powerful in liquid-based oligonucleotide assays. Since their discovery in the late 1990s, there has been increasing interest in integrating them into microarray-based platforms where they are immobilized on site-specific solid surfaces. Surface-tethered molecular beacons have, however, exhibited signal-to-background ratios as much as 10-20 times less than that exhibited by molecular beacons free in solution.

In solution-based hybridization assays, molecular beacons have shown high sensitivity and high specificity for target nucleic acid sequences, and they are able to generate fluorescence signals as high as 200-fold greater than their fluorescence background. However, the signal-to-background ratio is often significantly reduced when molecular beacon probes are immobilized on solid substrates as needed in a microarray format. Signal-to-background ratios from conventional surface-immobilized molecular beacon probes typically range from about 2 to 25. Surface immobilization can dominate molecular beacon probe-based sensor performance largely due to high backgrounds. Background fluorescence can occur because of non-specific interactions between the surface and molecular beacon probes, thereby disrupting the loop and stem structure and separating the fluorophore and quencher moieties. In addition, a change in electrostatic, steric and hydrophobic forces between the fluorophore and quencher moieties of probes attached to a solid surface can result in lower efficiencies of energy transfer between the fluorophore and quencher, resulting in higher background fluorescence.

As disclosed herein, molecular beacon probes were tethered to surface-patterned PEG microgels synthesized by focused electron irradiation where the edge of each microgel is highly diffuse and consists of very loosely confined PEG molecules in conformations as close as possible to those free in solution. Using molecular beacon probes tethered by biotin-streptavidin binding, signal-to-background ratios ranging from 40 to 50 were obtained. These values are only a factor of 2-3 less than those manifested by the same probes untethered in solution. The microgel-tethered molecular beacons also exhibited strong specificity when incubated with mixtures of synthetic oligonucleotide targets. For example, methicillin-resistant and methicillin-susceptible *Staphylococcus aureus* were distinguished from each other using target solutions created by asymmetric PCR initiated with DNA isolated from the bacterial lysates. Because of the 3-D nature of these microgels, the density of probes displayed per unit area of substrate surface exceeds the limit where probes tethered on a flat surface would otherwise interfere with each other. This feature, together with the submicron size of the microgels enabled target detection at concentrations as dilute as 100 pM. Surface tethering using electron beam patterned microgels thus not only achieves site-specific surface localization of molecular beacon probes at submicron length scales but simultaneously increases the signal, due to the high local probe concentration, and decreases the background, due to the near-liquid like character of the microgel surface. This represents a significant advance in the coupling of self-reporting molecular beacon probes to a microarray format.

Molecular beacon probes that can be used in this invention include those known in the art. In addition, one can design a molecular beacon probe using techniques known in the art. For example, a detailed protocol for the synthesis and purification of molecular beacon probes is available at www.molecular-beacons.org. As mentioned above, the probes contain single-stranded hairpins having a central single-stranded loop flanked by arms with interacting labels that form a double-stranded stem (a first or closed conformation) in the absence of target, thereby bringing the labels into interacting relationship; but that open when the loop binds to its target (a second conformation), thereby separating the labels and leading to a detectable signal.

Molecular beacon probes may be oligonucleotides labeled on one end with a fluorescent label, for example, a fluorophore or an intercalating dye, and on the other end with a moiety capable of quenching fluorescence from the fluorophore or other fluorescent label, for example a non-fluorescent quencher such as Dabcyl or a Black Hole Quencher. For example, oligonucleotide molecular beacon probes may be DNA, RNA or mixtures of DNA and RNA. They may include non-natural nucleotides and nucleotide analogs, for example LNA, PNA or 2' o-methyl RNA nucleotides. They may include non-natural internucleotide linkages. The target-recognition sequence, the loop, may interact with a nucleic acid target sequence, DNA or RNA, by hybridization. The loop may otherwise interact with a protein or peptide sequence, as is the case with aptamer beacons. In the case of aptamer beacons, the loop may be an oligonucleotide as described, for example, in Hamaguchi et al. (2001) Anal. Biochemistry 294: 126-131, or it may be a peptide sequence, as described in Thurley et al. (2007) J. Am. Chem. Soc. 129: 12693-12695. Devices according to this invention include arrays in which different areas include different molecular beacon probes, that is, probes with different loops for binding to different targets. Many different molecular beacon probes can be included in an array or microarray according to this invention.

Microgel and Gel-Tethered Molecular Beacon Probes

The invention also provides conjugates or structures to which the above-mentioned molecular beacon probes are tethered to discrete areas of gel, including microgel, or of a gel or gel-like coating. Preferred structures are electron-beam surface-patterned microgels attached on discrete areas in an array. The number of discrete areas in the array or microarray can range from few, for example, two or ten, to very many, for example, hundreds or thousands or even millions.

Structures or conjugates useful in this invention include, or have coatings that are, hydrophilic and gel-like. As used herein the term "gel" refers to aqueous gel of one or more macromolecular substances that form a gel with water under physiological conditions of temperature and pH. Such microgels preferably have the ability to swell and absorb fluid while maintaining a strong integral structure. Preferably, the microgel is substantially insoluble in water under physiological conditions, whereby the microgel is not washed away by water. The terms "gel" and "gel-like" are also used herein in the broad sense of the IUPAC definition of a gel: a non-fluid colloidal network or polymer network that is expanded throughout its whole volume by a fluid.

The terms "gel" and "microgel" simply differentiate the size of areas of the structure. The term "microgel" is used herein to refer to structures with an equivalent diameter of 10-10,000 nm, that is, in the nm and micrometer ranges. Structures useful in this invention have diffuse surfaces; that is, they include a discernable transition region going from the aqueous phase to the bulk gel phase, that is, pure hydrated gel, in which the structure gradually becomes more and more gel-like. Herein, "pure hydrated gel" refers to that portion of a gel with the highest crosslink density, which presumably is at or close to the center of the gel or microgel; or in cases where the gel or microgel has a region with a relatively homogeneous crosslink density at and near its center, that portion of the gel with the average crosslink density of the homogeneous region. Preferably, the transition region has a thickness that at least equals the maximum length of the probe. More preferably, the transition region has a thickness that at least equals the combined size of the probe and probe application materials; that is, functional moiety or moieties used to tether the probe to the surface. Most preferably, the transition region has a thickness that at least equals the combined size of the probe, the tethering moiety or moieties, and the biological material targets. Gel and gel-like coatings useful in the invention, in addition to being hydrophilic, do not act in a significantly deleterious way with the probes, the biological targets, or the probe application and tethering molecules. By "significantly deleterious", it is meant that the signal-to-background ratio of a molecular beacon probe in solution detection should not be more than five times higher than the signal-to-background ratio of the probe in detection when tethered to the surface of the structure, preferably not more than three times higher, and most preferably not more than two times higher.

In certain preferred embodiments, the present invention relates to molecular beacons tethered to electron-beam surface-patterned microgels. Some embodiments of the invention use microgels both created and covalently bonded to silicon substrates using focused-electron radiation of biotinylated poly(ethylene glycol), and with biotinylated molecular beacons immobilized thereon via a streptavidin-biotin interaction. In other embodiments of the invention, gels and microgels can be made by photo or thermal mechanisms of crosslinking and can be patterned on a surface by a number of different lithographic processes such as UV photolithography. In other embodiments of the invention, microgels are made from other polymers or oligomers using other mechanisms of molecular-beacon binding to the gels. In some embodiments of the invention, the crosslink density of the microgels gradually approaches zero at the extreme edge of each microgel at the interface between the microgel and the surrounding aqueous medium. In such embodiments of the invention, the molecular beacon probes are tethered away from the underlying solid surface, thus minimizing potentially detrimental molecular beacon interactions with that surface; and the molecular beacon probes are tethered to the diffuse microgel/medium interface and are localized in an environment that is as waterlike as possible. These tethering conditions lead to high signal and low background when the tethered molecular beacons hybridize with a complementary target. Furthermore, different microgels can be functionalized with different molecular beacons in order to achieve a site-specific distribution of molecular beacons. Such microgel-tethered molecular beacons can be used as probes to interact with oligonucleotide targets from several different sources which may or may not require amplification by PCR, NASBA or some other DNA or RNA amplification mechanism.

The immobilization of molecular beacon probes to solid surfaces by way of an intermediary water-like region can be realized with a variety of gels or gel-like surfaces depending on the structure of the gel at the gel-water interface. An important requirement is that the interface between the water and the gel or gel-like surface coating needs to be discernibly diffuse, preferably over a length scale at least as large as the size of the molecular beacon probes; more preferably over a length scale at least as large as the combined size of the molecular beacon probes and whatever functional moieties are used to bind the probes to the underlying gel; and most preferably over a length scale at least as large as the combined size of the probes, the target DNA, RNA or protein, and whatever functional moieties are used to bind the molecular beacon probes to the underlying gel. In the case of the e-beam patterned microgels that are exemplified, those functional moieties comprise a biotin-streptavidin complex. One preferred way to create a diffuse transition region is to reduce crosslink density progressively going from the pure hydrated gel to the aqueous phase.

Figure 8:
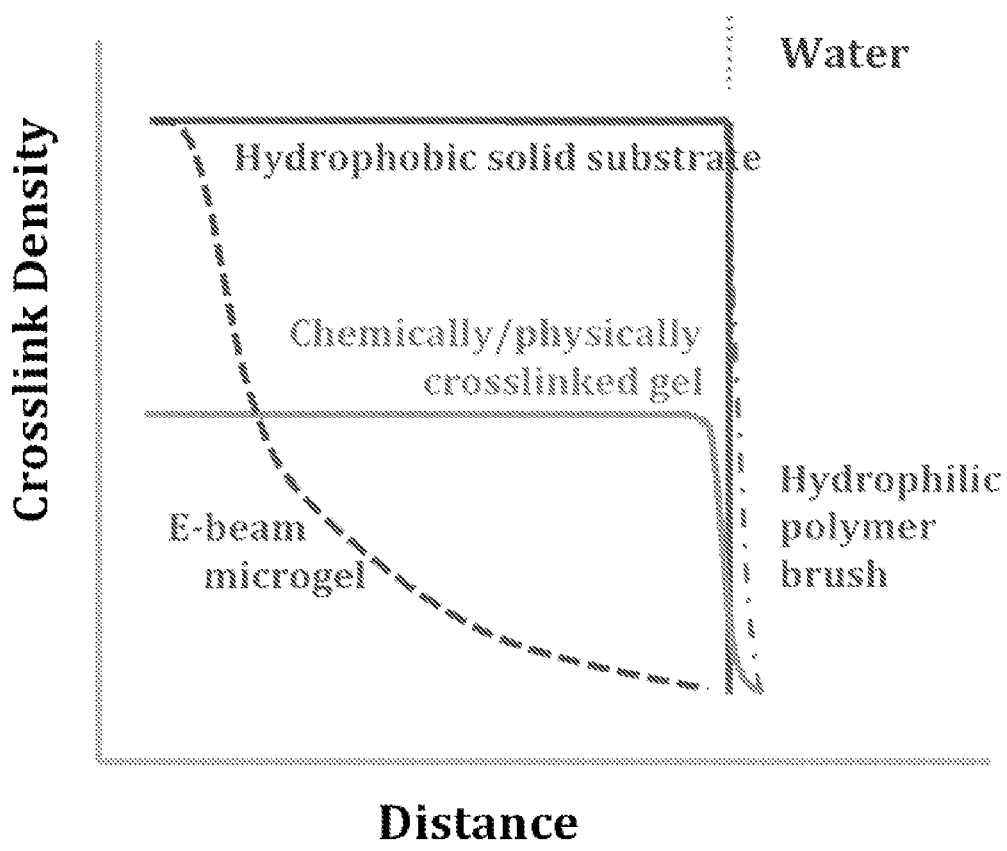
FIG. 8 is a graph depicting the transition region between the aqueous phase and the pure hydrated gel or gel-like coating, showing how crosslink density decreases as one moves outwardly from the center of the pure hydrated gel.

Differences in surface structure between electron-beam patterned microgels and other gels and gel-like surfaces are illustrated in FIG. 8. This figure schematically illustrates the concentration of crosslinks as a function of position moving from the center of a gel to its surface and then into the surrounding aqueous medium, which may, for example, be pure water, buffer, or some other aqueous solution. At one extreme is a typical hydrophobic solid substrate where the crosslink density of the gel is quite constant, and transition in gel-like properties, in the depicted case crosslink density, from the substrate to water is relatively abrupt, not diffuse. If such a surface is modified with some form of hydrophilic polymer brush, then there is a diffuse transition region from the pure solid substrate to the surrounding water, as indicated graphically in FIG. 8. The thickness or length and nature of the transition region depend on the packing density, molecular weight, and molecular architecture of the molecules used to form the brush. Such brush structures can be fabricated in a number of ways including polymerization from the surface, self-assembly, or grafting. Alternatively, gels and gel coatings can be created by a variety of chemical and physical crosslinking methods, some of which can include patterning by, for example, lithographic photopolymerization. These gels and gel coatings are differentiated from brushes by the fact that all three dimensions in a gel are at least a few times larger than the average mesh size of the gel. The average crosslink density and the chemical properties of the gel itself determine the equilibrium water concentration in such gels. In the case of gels and gel coatings, the transition region from pure hydrated gel to the surrounding water can be larger than that of a polymer brush. The physical extent of this transition region will depend on such parameters as the average gel mesh size, which is related to the distance between crosslinks, and surface-induced variations in composition or crosslink density. The transition zone in electron-beam patterned microgels is, as also shown in FIG. 8, greater still, because of the delocalization of energy deposition during the crosslinking process.

Similar electron-beam processing is used in the practice of electron-beam lithography, commonly used in the manufacture of semiconductor devices, and, in that community, such delocalization is referred to as the proximity effect. Proximity effects are also observed in many device-manufacturing technologies when patterning is achieved by optical photolithography, and these lead to patterns that are broadened due to diffraction and the effects of resolution limits. In the context of patterned microgel formation, proximity effects that lead to a delocalization of energy deposition can produce relatively diffuse transition regions between hydrated gel and the surrounding aqueous solution.

Gels can be made from many different materials, and the relatively high performance of molecular beacons tethered to gels can in principle be achieved with any number of different gel materials. The important characteristics of the gel material are that it must be hydrophilic and it must not itself interact in a significant way with the molecular beacon probes, the oligonucleotide targets, or other molecules that may be found in solutions used to create or apply the gel-tethered molecular beacons. Poly(ethylene glycol) is particularly effective because it is both hydrophilic and because it exhibits relatively weak intermolecular interactions with most molecules. Molecular beacons could, however, be tethered to other gels synthesized from either natural polymers, manmade polymers, or hybrids of the these including such materials as polyacids, polybases, and polymers derived from carbohydrates or saccharides.

Molecular beacons can be tethered to gels using a number of different linking moieties. These can be incorporated into the gel chemically (e.g., by copolymerization) or physically (e.g., by entrapment in the gel). The linking moieties can be located at the ends or within molecules within the gels. The concentration of such linkages, particularly in the vicinity of the gel-water interface, can be controlled and will in part determine how many molecular beacon probes can be tethered to a particular gel. These linking moieties must both have sufficient binding strength and specificity to bind molecular beacon probes. Biotin is one such moiety. Other possible linking moieties include amines, thiols, carboxyls, maleimides, carbodiimides, acrylates, and epoxides, among others, many of which are commonly known in the literature (see, for example, "Bioconjugate Techniques," by Greg T. Hermanson, BIOCONJUGATE TECHNIQUES, Second Ed., Elsevier (Academic Press) (2008)).

The submicron size of individual electron-beam patterned microgels together with the ability to pattern them on surfaces at inter-gel spacings of a few micrometers or less enables the formation of preferred arrays of microgel-tethered molecular beacons. The formation of arrays of surface patterned gels such that different gels are functionalized with molecular beacons that probe different oligonucleotide targets requires a method to deliver different molecular beacon probes to different gels. When the inter-gel spacing is relatively large, such differential functionalization can be achieved using established methods such as the microspotting technology used to create DNA microarrays. However, when the spacing between gels or microgels is a few microns or less, the resolution of existing spotting technologies is insufficient to differentially functionalize adjacent gels or microgels.

A new method that can differentially functionalize adjacent and closely spaced microgels exploits a variation of dip-pen nanolithography. In this method a sharp tip typical of the probes used in atomic force microscopy is coated with a solution of molecular beacons. In the dip-pen nanolithography literature such a solution is referred to as an ink. The ink solution is allowed to dry. The tip is then positioned over a specific microgel and lowered so that the tip touches the microgel. In contrast to typical methods using microarray spotters, this approach uses a dry tip and thus avoids spreading of the molecular beacon solution on the surface around the particular location of specific interest. And, in contrast to established methods of dip-pen nanolithography that use a dry ink, contacting the tip to a microgel provides a source of water that aids in the transfer of dry ink from the tip to the microgel. Established methods of dry-ink, dip-pen nanolithography are believed to involve the formation of a meniscus of water between the dry tip and the hard substrate where the water in the meniscus comes from ambient water on the hard surface and/or from ambient humidity. Such a meniscus is believed to facilitate transfer of the molecular beacon probes to the surface. In the case of functionalizing a microgel, water is available directly from the water bound to the microgel. Under ambient conditions the microgel provides an amount of water that is not available when a pen tip with dried ink interacts with a hard surface that has no gel coating. The small size of the probe tip limits the contact to an area of a few micrometers or less including submicron contact areas. Water from the microgel facilitates beacon transfer from the dried tip to the microgel. The fact that the amount of water available is proportional to the size of the microgel limits the extent to which the molecular beacons can spread around the microgel. Spreading is further limited by the fact that the surface surrounding the microgel is no more hydrophilic, and is usually much less hydrophilic, than the hydrogel itself. Hence, individual microgels can be functionalized. Different molecular beacon inks can be used to functionalize different microgels, that is, different discrete areas of the array, even when these microgels are as close together as a few micrometers or less.

Arrays

Also provided in the invention is a biochip or array, including microarrays, of tethered molecular beacon probes and their use in detection of biological target materials, including nucleic acids. Arrays and microarrays useful in the invention comprise a material having a major surface containing discrete, separated areas containing structures to which the probes are tethered. Preferably, the major surface is planar. Suitable materials include glass slides, polymeric sheets, and silicon wafers. Discrete areas can be depressions or wells in the major surface, areas created by a pattern of walls or dams affixed to the surface, or discrete structures affixed to the surface.

The biochip/array may contain a solid or semi-solid substrate having an attached gel-tethered molecular beacon probe or plurality of such molecular beacon probes described herein. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a pathogen or single disorder appreciated by those in the art. The probes may either be synthesized first, with subsequent attachment to the biochip, or may be directly synthesized on the biochip.

"Attached" or "immobilized" as used herein to refer to a nucleic acid (e.g., a probe), a gel, and a solid support substrate may mean that the binding between the gel-tethered probe and the solid support is sufficient to be stable under conditions of binding, washing, analysis, and removal. The binding may be covalent or non-covalent. Covalent bonds may be formed directly between the gel-tethered probe and the solid support or may be formed by a cross linker or by inclusion of a specific reactive group on either the solid support or the probe or both. Non-covalent binding may be one or more of electrostatic, hydrophilic, and hydrophobic interactions. Included in non-covalent binding is the covalent attachment of a molecule, such as streptavidin, to the support or gel and the non-covalent binding of a biotinylated probe to the streptavidin. Immobilization may also involve a combination of covalent and non-covalent interactions.

The solid substrate can be a material that may be modified to contain discrete individual sites appropriate for the attachment or association of the probes and is amenable to at least one detection method. Examples of such substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate can be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The array/biochip and the gel-tethered probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the gel by either the 5' terminus, 3' terminus, or via an internal nucleotide. The probe may also be attached to the gel non-covalently. For example, biotinylated oligonucleotides can be made, which may bind to surfaces covalently coated with streptavidin, resulting in attachment. Alternatively, probes may be synthesized on the surface using techniques such as photopolymerization and photolithography. Detailed discussion of methods for linking nucleic acids to a support substrate can be found in, e.g., U.S. Pat. Nos. 5,837,832, 6,087,112, 5,215,882, 5,707,807, 5,807,522, 5,958,342, 5,994,076, 6,004,755, 6,048,695, 6,060,240, 6,090,556, and 6,040,138.

In some embodiments, an expressed transcript (e.g., a transcript of a gene described herein) is a target of interest. In such embodiments, a set of binding sites can include probes with different nucleic acids that are complementary to different sequence segments of the expressed transcript. Examples of such nucleic acids can be of length of 15 to 200 bases, 20 to 100 bases, 25 to 50 bases, 40 to 60 bases. Each probe sequence can also include one or more linker sequences in addition to the sequence that is complementary to its target sequence. A linker sequence is a sequence between the probe sequence and the surface of the gel or support. For example, the nucleic acid arrays of the invention can have one probe specific to each target gene. However, if desired, the nucleic acid arrays can contain at least 2, 5, 10, 100, 200, 300, 400, 500 or more probes specific to some expressed transcript.

Kits

In another aspect, the present invention provides kits embodying the methods, compositions, and systems for analysis of presence of a target agent, e.g., a target nucleic acid sequence or gene expression as described herein.

Such a kit may contain a molecular beacon probe described herein together with any or all of the following: assay reagents, buffers, probes and/or primers, and sterile saline or another pharmaceutically acceptable emulsion and suspension base. In addition, the kit may include instructional materials containing directions (e.g., protocols) for the practice of the methods described herein. For example, the kit may be a kit for the amplification, detection, identification or quantification of a target sequence. To that end, the kit may contain a suitable primer (e.g., hairpin primers), a forward primer, a reverse primer, and a probe.

In one example, a kit of the invention includes one or more microarray slides (or alternative microarray format) onto which a plurality of different probes (each corresponding to one of the above-mentioned genes or targets) have been deposited. The kit can also include a plurality of labeled probes. Alternatively, the kit can include a plurality of polynucleotide sequences suitable as probes and a selection of labels suitable for customizing the included polynucleotide sequences, or other polynucleotide sequences at the discretion of the practitioner. Commonly, at least one included polynucleotide sequence corresponds to a control sequence, e.g., a normalization gene or the like. Exemplary labels include, but are not limited to, a fluorophore, a dye, a radiolabel, an enzyme tag, that is linked to a nucleic acid primer.

In one embodiment, kits that are suitable for amplifying nucleic acid corresponding to a target nucleic acid sequence are provided. Such a kit includes reagents and primers suitable for use in any of the amplification methods described above. Alternatively, or additionally, the kits are suitable for amplifying a signal corresponding to hybridization between a probe and a target nucleic acid sample (e.g., deposited on a microarray).

In addition, one or more materials and/or reagents required for preparing a biological sample for gene expression analysis are optionally included in the kit. Furthermore, optionally included in the kits are one or more enzymes suitable for amplifying nucleic acids, including various polymerases (RT, Taq, etc.), one or more deoxynucleotides, and buffers to provide the necessary reaction mixture for amplification.

Typically, the kits are employed for analyzing gene expression patterns using RNA as the starting template. The RNA template may be presented as either total cellular RNA or isolated mRNA; both types of sample yield comparable results. In other embodiments, the methods and kits described in the present invention allow quantitation of other products of gene expression, including tRNA, rRNA, or other transcription products.

Optionally, the kits of the invention further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

The kits optionally contain distinct containers for each individual reagent and/or enzyme component. Each component will generally be suitable as aliquoted in its respective container. The container of the kits optionally includes at least one vial, ampule, or test tube. Flasks, bottles and other container mechanisms into which the reagents can be placed and/or aliquoted are also possible. The individual containers of the kit are preferably maintained in close confinement for commercial sale. Suitable larger containers may include injection or blow-molded plastic containers into which the desired vials are retained. Instructions, such as written directions or videotaped demonstrations detailing the use of the kits of the present invention, are optionally provided with the kit.

In a further aspect, the present invention provides for the use of any composition or kit herein, for the practice of any method or assay herein, and/or for the use of any apparatus or kit to practice any assay or method herein.

A "test sample" or a "biological sample" as used herein may mean a sample of biological tissue or fluid therefrom that comprises a molecule of interest, such as peptides and nucleic acids. Such samples include, but are not limited to, tissue or body fluid isolated from animals. Biological samples may also include sections of tissues such as biopsy and autopsy samples, frozen sections taken for histological purposes, blood, plasma, serum, sputum, stool, tears, mucus, urine, effusions, amniotic fluid, ascitic fluid, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used. The term "body fluid" or "bodily fluid" refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample: for example, the sample may be frozen at about −20° C. to about −70° C.

The term "gene" used herein refers to a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto. The term also includes pseudogenes, which are dysfunctional relatives of known genes that have lost their protein-coding ability or are otherwise no longer expressed in a cell.

"Nucleic acid" or "oligonucleotide" or "polynucleotide" as used herein refers to at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions. Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

The term "primer" refers to any nucleic acid that is capable of hybridizing at its 3' end to a complementary nucleic acid molecule, and that provides a free 3' hydroxyl terminus which can be extended by a nucleic acid polymerase. As used herein, amplification primers are a pair of nucleic acid molecules that can anneal to 5' or 3' regions of a gene (plus and minus strands, respectively, or vice-versa) and contain a short region in between. Under appropriate conditions and with appropriate reagents, such primers permit the amplification of a nucleic acid molecule having the nucleotide sequence flanked by the primers. For in situ methods, a cell or tissue sample can be prepared and immobilized on a support, such as a glass slide, and then contacted with a probe that can hybridize to RNA. Alternative methods for amplifying nucleic acids corresponding to expressed RNA samples include those described in, e.g., U.S. Pat. No. 7,897,750.

The term "probe" as used herein refers to an oligonucleotide capable of binding to a target (e.g., a target nucleic acid of complementary sequence) through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

"Stringent hybridization conditions" as used herein refers to conditions under which a first nucleic acid sequence (e.g., probe) hybridizes to a second nucleic acid sequence (e.g., target), such as in a complex mixture of nucleic acids. Stringent conditions are sequence-dependent and be different in different circumstances, and can be suitably selected by one skilled in the art. Stringent conditions may be selected to be about 5-10° C. lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C. However, several factors other than temperature, such as salt concentration, can influence the stringency of hybridization and one skilled in the art can suitably select the factors to accomplish a similar stringency.

As used herein, the signal-to-background (SBR) ratio in connection with microgel-tethered molecular beacon-target hybridization refers to a ratio obtained according to the method described in Example 3 below. As used herein the term "reference" value (e.g., reference a SBR ratio or a reference percentage thereof) refers to a value that statistically correlates to a particular outcome when compared to an assay result. In preferred embodiments, the reference SBR ratio value is determined from statistical analysis of studies that compare untethered one or more molecular beacon probes in solution. The reference value may be a threshold score value or a cutoff score value. Typically a reference value will be a threshold above (or below) which one outcome is more probable and below which an alternative threshold is more probable.

The examples below disclose various molecular beacons that were immobilized on electron-beam (e-beam) patterned biotinylated poly(ethylene glycol) (biotinylated-PEG) microgels through a streptavidin-biotin interaction. The diameter of each e-beam patterned hydrated microgel was as small as about 400 nm, roughly 10 to 100 times smaller than a spot in a typical microarray. Monte Carlo simulation of electron-polymer interactions showed that the crosslink density within each of these e-beam patterned microgels decreases as a function of distance from the microgel center and, in addition, that the edge of each microgel consists of a highly diffuse interface of very loosely grafted PEG molecules to which the molecular beacons are tethered.

As shown in the examples, microgels conjugated with three gel-tethered molecular beacons were successfully used in detecting and identifying methicillin resistance in *Staphylococcus aureus* (MRSA, Sinsimer et al. *J. Clin. Microbiol.,* 2005, 43, 4585-4591). One molecular beacon probe identifies a region in the 16s rRNA gene (bac16S), which is common to all bacteria. Another molecular beacon probe identifies a region in the protein A gene (spa), which is present in all *S. aureus* species. The third molecular beacon identifies a region in the mecA gene, which is unique to only MRSA strains.

Example 1

Microgel-Tethering of Molecular Beacon Probes

In this example, assays were carried out to examine physical properties of microgel-tethered with molecular beacon probes.

For the specific electron-irradiation conditions used in the present experiments, the size of each hydrated microgel was approximately 400 nm in diameter and 100 nm in height (FIG. 1A). The microgels swelled primarily in the direction perpendicular to the substrate (FIG. 1B). The 50 fC point dose of 2 keV electrons created a PEG microgel that resists non-specific protein adsorption. Note that the substrate surface between gels consists of a PEG-like grafted silane, which also resists non-specific protein adsorption.

FIG. 2 illustrates the operation of microgel-tethered molecular beacons. Each molecular beacon probe is tethered to a microgel via a biotin-streptavidin bond. When no target nucleic acid is present, the molecular beacon probe is in its hairpin conformation, placing the fluorophore and quencher in close proximity, and no fluorescence is emitted (FIG. 2A). When a molecular beacon probe hybridizes to a complementary target nucleic acid, the molecular beacon undergoes a conformational rearrangement, separating the fluorophore and quencher and causing the probe to fluoresce (FIG. 2B). Typical fluorescence images of microgel-tethered molecular beacon probes, before and after incubation with a target oligonucleotide, are shown in FIGS. 2C and 2D, respectively. The spatial distribution of the fluorescence in FIG. 2D corresponds to the positions of the patterned microgels, and this demonstrates that the 2 keV/50 fC electron radiation is sufficient to form a surface-bound PEG microgel but is a sufficiently low dose that the activity of biotin groups is retained.

To better understand how streptavidin molecules and molecular beacon probes are distributed on a microgel, assays were carried out to determine the average number of streptavidins and the average number of molecular beacon probes per microgel. Using a standard curve of fluorescence intensity from solutions containing known concentrations of Texas-red labeled streptavidin molecules, the number of streptavidins per single microgel was determined as approximately 10,700 (FIG. 3). This number is in good agreement with a simple estimate where it was assumed that each microgel is a cylinder with a diameter of 400 nm and height of 100 nm and that each streptavidin molecule has dimensions of 4.5×4.5×5.0 nm. If the streptavidins cover the microgel surface as a close-packed monolayer on a single plane, one would expect this surface to contain about 11,000 to 12,000 streptavidin molecules.

Similarly, using a standard curve derived from known concentrations of Texas-red labeled hairpin oligonucleotides with no quencher moiety, the average number of molecular beacon probes per single microgel was determined as approximately 11,800 (FIG. 3). This number corresponds to 46,900 probes/$\mu m^2$ if the hydrated microgel is modeled as a cylinder as described above. Immobilized single-stranded DNA probes with lengths of 25 bases have been reported to exhibit reduced hybridization efficiency at a surface density higher than 50,000 molecular beacons/$\mu m^2$. In this example, if the 11,800 molecular beacons, which have a 28 bases capture loop, are projected onto a circular area with a radius of 0.2 μm, corresponding to the footprint of an individual microgel, the areal density would be 94,000 probes/μm² and could lead to a reduced hybridization efficiency. However, in contrast to many surface-immobilization strategies that provide a two-dimensional presentation of DNA probe molecules, surface-patterned microgels here are three-dimensional and probes can be tethered both to the microgel top and to the microgel sides. Since it was found that the number of molecular beacon probes is comparable to the number of streptavidins, there is on average only one molecular beacon probe bound to each streptavidin molecule. The average intermolecular beacon distance thus corresponds to the size of one streptavidin molecule, which is about 5 nm.

Example 2

Solution-Based Molecular Beacon-Target Hybridization

In this example, assays were carried out to examine solution-based molecular beacon-target hybridization.

The performance of molecular beacon probes free in solution has typically been reported to be much higher than that of molecular beacons tethered to a variety of solid substrates. As a reference point, experiments were carried out to measure the performance of the mecA, spa, and bac16S molecular beacons in solution. The experiments were carried out in the same buffer conditions used for hybridization experiments with the microgel-tethered molecular beacons. This buffer composition is similar to those used in PCR assays described below. Table 1 summarizes the signal-to-background ratios determined for each of the three molecular beacons when exposed to their complementary oligonucleotide targets sequences (see Table 2). For each, three levels of fluorescence intensity were recorded in sequence as $I_{buffer}$, $I_{MB}$ and $I_{MB+target}$ which correspond respectively to the background fluorescence intensity of the hybridization buffer alone, the fluorescence intensity of the solution after addition of the molecular beacon probe, and the fluorescence intensity of the solution after addition of the oligonucleotide target. The signal-to-background ratio in solution, $SBR_{soln}$ was defined as below:

$$SBR_{soln} = \frac{(I_{MB+target} - I_{buffer})}{(I_{MB} - I_{buffer})} \quad (1)$$

Typical signal-to-background ratio values range from 100 to 120.

Example 3

Microgel-Tethered Molecular Beacon-Target Hybridization

In this example, microgel-tethered molecular beacon-target hybridization was examined. To quantitatively characterize the performance of the microgel-tethered molecular beacon probes, the signal-to-background ratio on the surface ($SBR_{gel}$) is defined as the following:

$$SBR_{gel} = \frac{(I_{MB+target}^{gel} - I_{MB+target}^{bkg})}{(I_{MB}^{gel} - I_{MB}^{bkg})} \quad (2)$$

where $I_{MB+target}^{gel}$ and $I_{MB}^{gel}$ are the average fluorescence signal per microgel after exposure to target (FIG. 2D) and to buffer (FIG. 2C), respectively. $I_{MB+target}^{bkg}$ and $I_{MB}^{bkg}$ are the corresponding average fluorescence signals emitted by an equivalent area from the unpatterned surface surrounding the array of microgels, after addition of the target and after exposure only to buffer, respectively. The results are summarized in Table 1. Such direct comparisons of signal-to-background ratios between dissolved and immobilized molecular beacons have rarely been reported. The average signal-to-background ratio values for the microgel-tethered molecular beacons range from about 40 to 50. These values are substantially higher than those exhibited by many other molecular beacon immobilization platforms and they are only a factor of 2 to 3 less than those measured using molecular beacons unconstrained by a substrate. The signal-to-background ratio of the gel-tethered molecular beacons can be further enhanced since many other factors—such as the sequences of the molecular beacon probes and target nucleic acids, the lengths of molecular beacon arm and loop sequences, and the hybridization conditions—can all affect both the signal and the background.

TABLE 1

Signal-to-background ratios of molecular beacon probes in solution and tethered to surface-patterned microgels.

| Molecular beacon | In solution (hybridization at 50° C.) | Microgel tethered molecular beacons (hybridization at 50° C.) |
| --- | --- | --- |
| mecA | 100.2 ± 1.5 | 45.6 ± 8.1 |
| spa | 106.7 ± 1.5 | 61.1 ± 6.9 |
| bac16S | 124.8 ± 6.1 | 48.5 ± 4.0 |

In practice, target nucleic acids used for hybridization to a detection platform are often derived from DNA or RNA isolated from samples and subjected to a nucleic acid amplification step, such as the Polymerase Chain Reaction or Nucleic Acid Sequence Based Amplification assay. These amplification products are in general 80 to 200 nucleotides in length. Thus, assays were carried out to evaluate signal-to-background ratios of the microgel-tethered spa molecular beacon using complementary spa oligonucleotide targets with lengths of 60, 98 and 200-nucleotides (Table 3). No significant variation in the signal-to-background ratio values was observed. These were 61.1±6.9 for the 44-nucleotide target, 62.1±15.0 for the 60-nucleotide target, 68.1±12.5 for the 98-nucleotide target, and 49.6±6.8 for the 200-nucleotide target. These results demonstrate that the microgel-tethered platform is thus well suited to the detection and identification of target nucleic acid generated during a nucleic acid amplification step.

Example 4

The Diffuse Nature of the Microgel-Water Interface

A particularly important aspect of the microgels is the fact that they can be made by a focused e-beam radiation-crosslinking process. By its very nature, this process creates a variable crosslink density that is lowest at the edges of each microgel, since this is the region where the incident electrons deposit the least amount of energy. Furthermore, since the deposition of energy is a stochastic process, the surface of each microgel is rough and diffuse over length scales comparable to the size of an individual molecular beacon. To illustrate these ideas, a Monte Carlo approach was used to simulate electron trajectories and the spatial distribution of energy deposited during irradiation.

Figure 4:
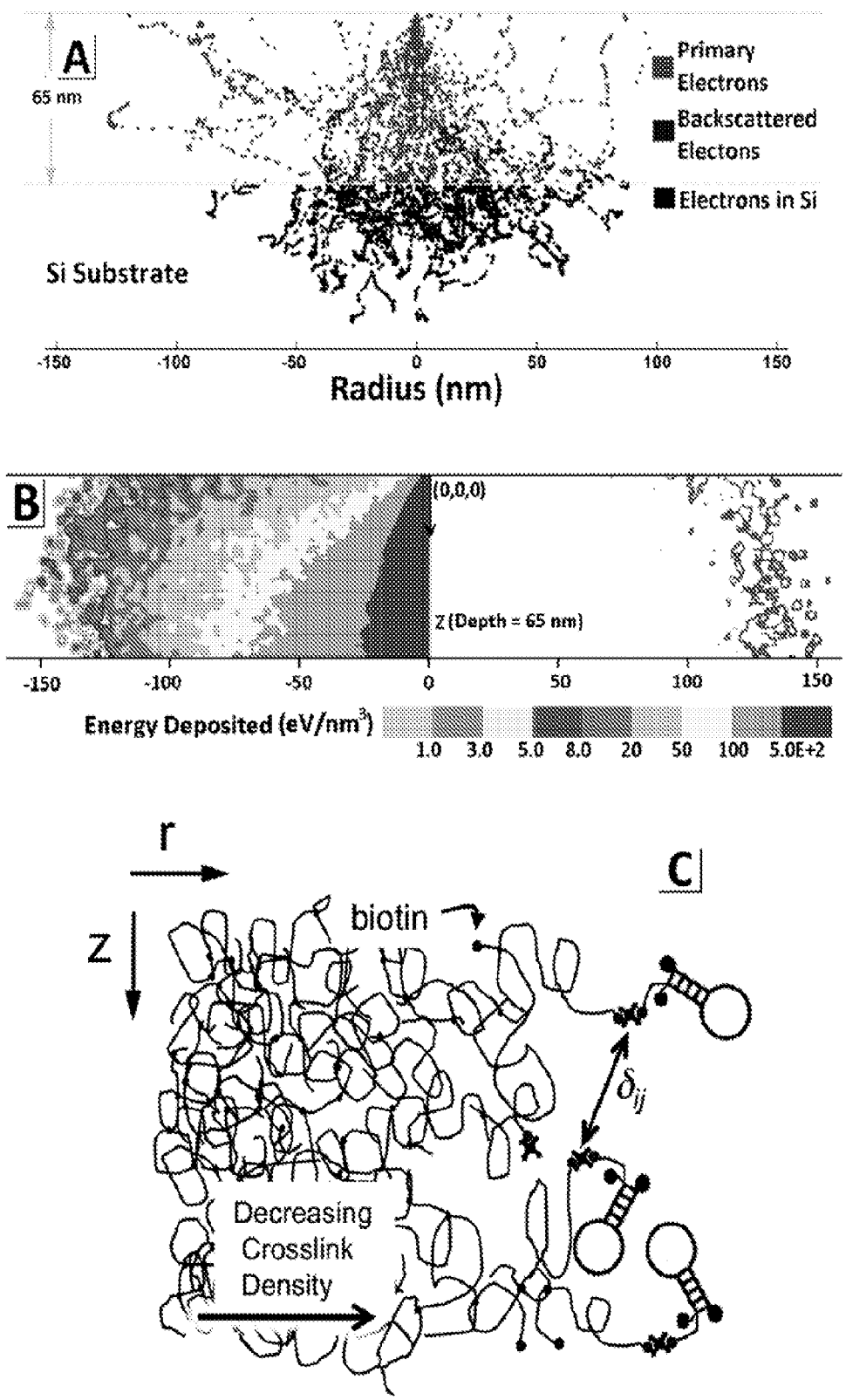
FIGS. 4A-C are as set of diagrams showing the results of a Monte Carlo simulation of 2 keV electrons incident on a 65 nm thick PEG film showing: (A) a Z-R section of the trajectories from a 100 electron simulation; (B) the energy deposition for a 320,000 electron simulation where the left half presents a large range of energy contours while the right half isolates only those voxels with the threshold energy needed for crosslinking; and (C) schematically the decreasing crosslink density with increasing radial distance from the microgel center at the extreme edge of the microgel where individual molecules are grafted to large-mesh gel.

FIG. 4 shows the results of one such simulation for a focused pulse involving 50 fC of 2 keV electrons incident on a 65 nm thick polymer film resting on a silicon substrate. Because of the relatively low incident energy, the electrons interact strongly with the polymer film and lose most of their energy before reaching the substrate. FIG. 4A illustrates typical electron trajectories. The primary electrons (colored red) traverse the polymer film, and their trajectories are broadened by elastic scattering. Energy from primary electrons that reach the substrate (colored black) drives the radiation chemistry, which binds the PEG to the underlying substrate, but energy deposited in the substrate has little, if any, effect on the polymer film. Electrons backscattered from the substrate into the polymer film (colored blue) deposit energy at relatively large distances from the incident beam and effectively degrade the spatial resolution of e-beam patterning. FIG. 4B illustrates the energy deposited per unit volume along a particular Z-R plane. This left portion of this figure depicts the entire range of deposited energies, while for R>0 only those energies corresponding to the threshold for crosslinking are shown. The amount of energy deposited is greatest along the path of the incident e-beam. For this innermost column of material, one can expect an extremely high crosslink density. In this region there may also be significant chemical changes in the polymer due to sputtering and other radiolytic processes. Since this column is contained within the core of the overall microgel, it has little effect on the gel surface properties. The core region may, however, play a key role in binding the microgel to the substrate. Moving radially away from this core region, the amount of deposited energy decreases by several orders of magnitude. One can expect the crosslink density will thus also significantly decrease.

It was estimated a threshold density of deposited energy required for crosslinking based on typical G values—the number of events per 100 eV of deposited energy—for hydrocarbon polymers reported in the literature. Values reported for crosslinking, $G_x$, of hydrocarbons range from about 0.5 to 5, depending on the polymer and the irradiation conditions. For the purposes of the model here, a value of 2 was assumed. Given the density of PEG as 1.05 g/cm$^3$ together with the molecular weight of 5000 g/mole, the threshold energy density for crosslinking would be about 6 eV/nm$^3$. The purple color on FIG. 4B denotes the voxels in which the energy deposited per unit volume is 5 to 8 eV/nm$^3$ corresponding to the threshold energy density for crosslinking. This simulation thus predicts a microgel diameter slightly smaller than but nevertheless in reasonable agreement with that measured experimentally (about 400 nm). The discrepancy can be attributed in part to uncertainties in the $G_x$ value and to uncertainties in the Bethe stopping power expression (see eq. [3] in Experimental Session) for low-energy electrons. Nevertheless, the basic conclusions one can draw from this model do not depend significantly on these discrepancies.

Importantly, FIG. 4B shows that the contour of purple voxels corresponding to the threshold for crosslinking is highly nonlinear. This is a consequence of the statistical nature of electron scattering coupled to the fact that the flux of scattered electrons at a given depth, Z, in the polymer film and at given radius, R, from the column of electron incidence (R=0), decreases in a manner roughly proportional to 1/R$^2$. At small |R|, variations in the amount of energy deposited per voxel are not very important, since these voxels all receive amounts of energy well in excess of the minimum required for crosslinking and they are located relatively far from the microgel surface. At large |R|, voxels have either received insufficient energy for crosslinking or, for those voxels that have received the threshold amount, are surrounded by insufficiently crosslinked voxels. In this regime, insufficient gelation occurs, and polymer from this region, together with the surrounding unexposed polymer, is washed away during post-irradiation washing in a good solvent for PEG. In the intermediate regions, voxels receiving a threshold amount of energy are connected to other voxels that receive an amount of energy at or exceeding the threshold. Upon post-irradiation washing, polymer in these voxels would remain covalently connected to a continuous network. The crosslink density asymptotically approaches zero when going radially away from the center portion of the microgel, and, in the limit, the gel surface contains individual and fully hydrated PEG molecules with only one crosslink and with minimal conformational constraints imposed by the underlying gel (FIG. 4C). While molecular-weight effects were not examined as part of the present work, it is anticipated that increasing the molecular weight will further enhance these effects, since the crosslink density per unit volume will decrease with increasing molecular weight.

The effectiveness, as measured by their signal-to-background ratio, of microgel-tethered molecular beacons can thus be attributed to the fact that the gel environment creates conditions that approximate that of molecular beacons freely dissolved in an aqueous solution. The surface of an e-beam patterned PEG microgel is quite water-like. One important part of this water-like characteristic is due to the PEG itself. Homopolymer PEG is water soluble with its ether oxygen able to bind as many as 2 to 4 water molecules. In both gel and PEGylated-surface forms, PEG has been shown to resist the adsorption of most biomolecules and most cells. This antifouling behavior can be attributed to the fact that an adsorption event will have both an enthalpic cost due to the need to displace water bound to the PEG and an entropic cost due to the reduction of possible PEG segment conformations due to a binding event. It has been shown that e-beam patterned PEG microgels very effectively resist nonspecific protein adsorption, and *J. Am. Chem. Soc.*, 2009, 131, 521-527 . . . have demonstrated similar behavior in a number of e-beam patterned functionalized PEG microgels, including microgels patterned from biotinylated PEG. Another important part of the water-like characteristic of the microgel is the fact that there is a non-uniform spatial distribution of crosslinks which is necessarily highest at the point of incidence of the focused e-beam and decreases monotonically to zero in the radial direction away from the point of incidence. At the extreme edge of the microgel, where the tethered molecular beacon probes are most able to interact with complementary target molecules in solution, the microgel consists of a few PEG molecules only loosely grafted to each other and with the fewest possible number of conformational constraints. Such microgel structure is significantly different from that characteristic of, for example, photopolymerized gels such as those produced via UV lithographic techniques. In contrast to e-beam crosslinked microgels, photopolymerization would create a crosslink density that is either homogenous across the microgel or higher at the edge than at the center.

Example 5

Sensitivity of Microgel-Tethered Molecular Beacon Probes

Figure 5:
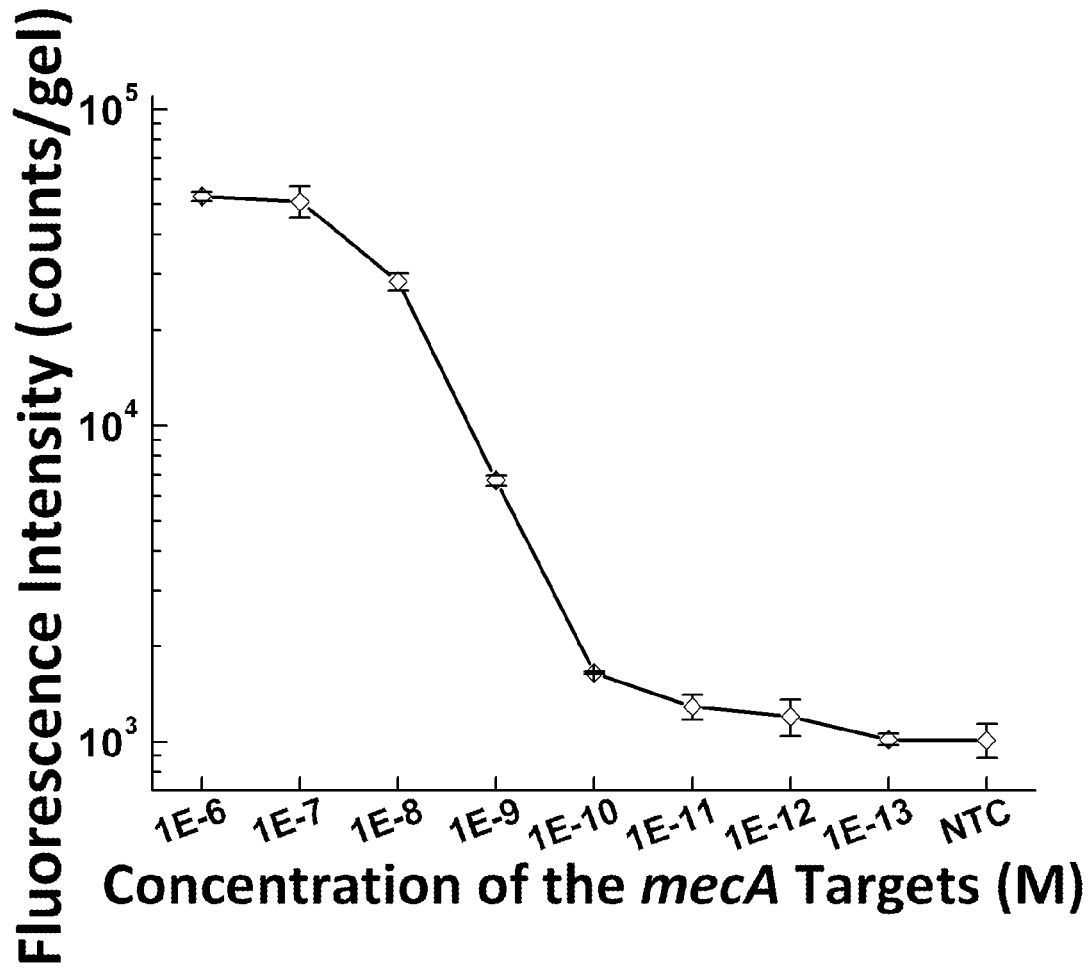
FIG. 5 is a plot of a titration curve showing the decrease in fluorescence intensity from microgel-tethered mecA molecular beacon probes as the concentration of its oligonucleotide target decreases. The detection limit for this platform is 100 pM. NTC=Negative control with no target.

In this example, the sensitivity of microgel-tethered molecular beacon probes was examined. FIG. 5 shows the fluorescence intensity of microgel-tethered mecA molecular beacon probes as the concentration of complementary oligonucleotide target decreases from $10^{-6}$ M to $10^{-13}$ M. The detection limit or platform sensitivity was defined as the target concentration which elicits a fluorescence intensity greater than the average intensity plus twice the standard deviation of the background (hybridization buffer alone). It was found that the background fluorescence intensity was 1,011 counts/microgel with a standard deviation of 126. The lowest target concentration eliciting a fluorescence intensity above the background threshold was 100 pM (1,650 counts/microgel). This sensitivity may be improved further by varying the number of microgels in the probing array, by adjusting the number of streptavidins on each microgel, and/or by adjusting the hybridization conditions—e.g. longer hybridization times or integrating this platform in dynamic fluid system.

Example 6

Specificity of Microgel-Tethered Molecular Beacon Probes

In this example, the specificity of microgel-tethered molecular beacon probes was examined. FIGS. 6A and 6B present representative images from an assay in which bac16S molecular beacon probes were bound to microgels patterned into specific designs. Any number of such user-defined patterns is possible due to the flexible afforded by modern electron-optical systems. The particular pattern illustrated by FIG. 6 consists of discrete microgels separated from each other by an inter-gel spacing of 0.4 µm. Since only bac16S molecular beacon probes were bound to this pattern, the molecular beacon probes tethered to it respond only to the bac16S target in solution. The data in FIG. 6A were collected after a pattern functionalized with bac16S molecular beacon probes was exposed to a solution containing 1 µM spa and 1 µM mecA oligonucleotide targets. Since there was no complementary bac16S target, a negligible signal was observed. In contrast, the data in FIG. 6B were collected after an identical pattern was exposed to a solution containing spa, mecA and bac16S oligonucleotide targets (1 µM each). This pattern exhibits an obvious fluorescence increase thus indicating the presence of the bac16S target.

FIG. 6C demonstrates the specificity of the platform. Biotinylated-PEG microgel arrays were functionalized with either the mecA, spa or bac16S molecular beacon probes. Each array was then incubated with a solution containing one, two or three target nucleotides (Table 2). The fluorescence intensities of the microgel-tethered mecA molecular beacon probes were normalized by the fluorescence intensity exhibited after incubation with a solution containing only the mecA oligonucleotide target. Similar, the fluorescence intensities of microgel-tethered spa and bac16S molecular beacon probes were normalized to those from solutions containing only the spa and bac16S oligonucleotide targets, respectively. This plot clearly shows that all three microgel-tethered molecular beacons exhibit excellent discrimination between the different oligonucleotide targets and that each is highly specific for its complementary target. Quantitatively, the maximum fluorescence intensity when the microgel-tethered bac16S molecular beacon was incubated with a solution containing the (mismatched) mecA oligonucleotide target was less than 11% of the total fluorescence intensity elected when the microgel-tethered bac16S molecular beacon was hybridized to its perfect complementary oligonucleotide target. This signal could be the result of non-specific hybridization of the mecA oligonucleotide target and the molecular beacon probe, which would cause the probe to fluoresce, or a non-specific interaction of the oligonucleotide with the gel matrix, which would cause a conformation change in the molecular beacon probe and also induce fluorescence. The highest non-specific fluorescence intensities observed for the microgel-tethered mecA and spa molecular beacon probes were less than 7 and 8%, respectively.

It was not observed that, despite the low fluorescence background, the presence of non-complementary oligonucleotide targets can reduce the maximum fluorescence intensity. For example, when the spa molecular beacon probes were incubated with a mixture of spa and bac16S oligonucleotide targets, the fluorescence intensity was only 46.2% of that when the molecular beacon array was incubated with a solution containing only its complementary spa target. It is possible that this signal decrease may be due to non-complementary targets binding non-specifically to the gel matrix preventing the complementary targets from hybridizing.

Example 7

Identification of PCR Generated Amplification Products

The total amount of target nucleic acids isolated from some sample is often very low, and the fluorescence signals generated by hybridization of the isolate target to a hybridization probe is therefore often not detectable. A common route in many detection assays is thus to include a nucleic acid amplification step, such as a Polymerase Chain Reaction (PCR) assay, and the microgel-tethering platform was tested using nucleic acid amplification products generated by PCR amplification. A previously developed assay was adopted, which includes PCR amplification of nucleic acid target sequences isolated from bacterial lysates to distinguish methicillin-sensitive *Staphylococcus aureus* (MSSA) from methicillin-resistant *Staphylococcus aureus* (MRSA). This assay is designed to detect: (i) a region of 16s RNA gene, which is conserved in all bacteria; (ii) a region of the protein A gene (spa), which is specific to *S. aureus*; and (iii) a region of the mecA gene, which confers resistance to methicillin. In other words, DNA isolated from a methicillin-sensitive strain will contain the 16s RNA and spa gene, but not the mecA gene. In contrast, a methicillin-resistant strain will contain all three genes. DNA isolated from bacterial lysates was amplified using an asymmetric PCR assay involving different concentrations of forward and reverse primers in order to generate single-stranded PCR products, which are ideal targets for DNA array platforms.

Figure 7:
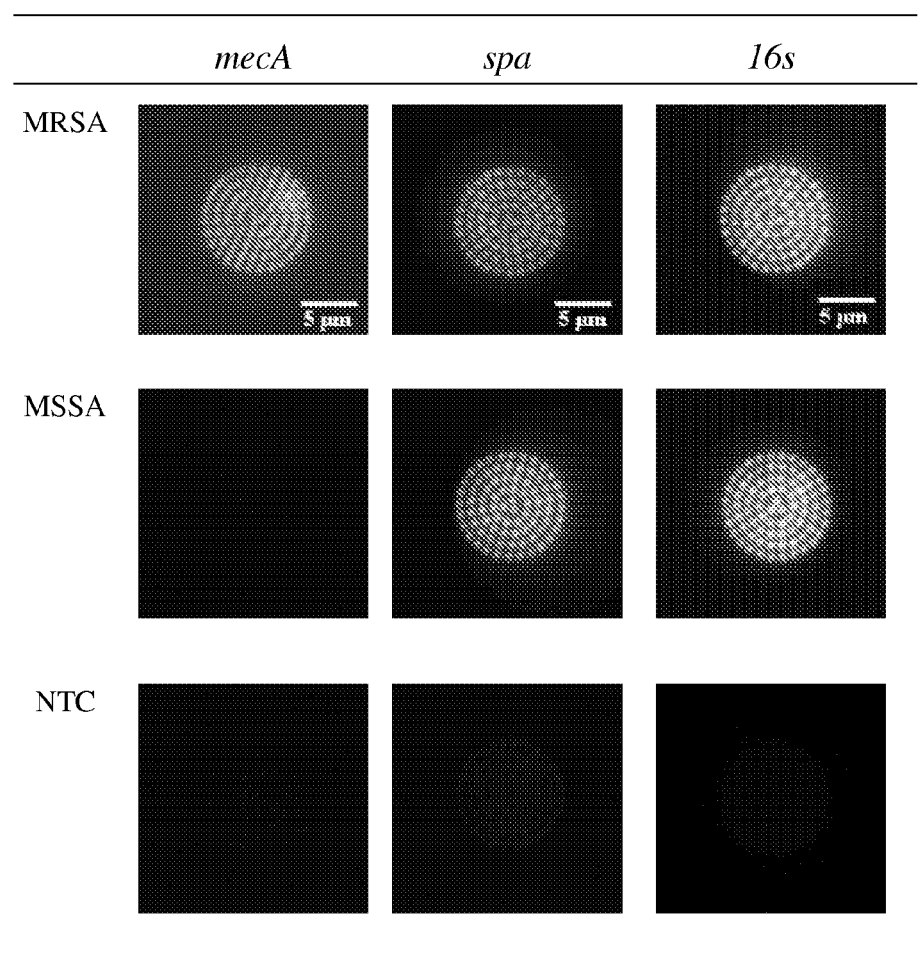
FIG. 7 is a set of photographs showing fluorescence images of microgels functionalized with mecA, spa, or bac16S molecular beacon probes. Methicillin resistant (MRSA) and sensitive (MSSA) *S. aureus* strains are identified using target nucleic acids amplified by PCR initiated with DNA isolated from bacterial lysates. MRSA is identified by the presence of mecA, spa, and bac16S target nucleic acids after PCR amplification and MSSA is identified by the presence of spa, and bac16S target nucleic acids, but absence of mecA nucleic acids. The negative control (NTC) shows that no fluorescence signal is present when no target nucleic acids are present after the PCR amplification steps.

FIG. 7 shows that arrays of gel-tethered molecular beacons are able to effectively discriminate between MSSA and MRSA. Amplification products generated from DNA isolated from MRSA lysates contain target sequences complementary to all three molecular beacon probes. Hence, the top row of images in FIG. 7 display high fluorescence for each of the probes. Amplification products generated from DNA isolated from MSSA lysates do not contain target sequences of the mecA gene, and, consequently, no fluorescence is elicited from the array of microgels functionalized with mecA molecular beacons (left panel, middle row of images). However, as anticipated, strong fluorescence is observed form microgels functionalized with the spa and bac16S molecular beacon probes (middle and right panel, middle row images). The lower row images shows three negative control arrays, which were incubated with PCR volumes initiated without any DNA template, and these do not show fluorescence. The measured intensities for the mecA, spa, and 16s negative controls were 2.1%, 4.3% and 3.4% of the maximum fluorescence intensities (positive controls), respectively.

Example 8

This example describes materials and methods used in EXAMPLES 1-7 above.

Oligonucleotide Synthesis

The molecular beacon probes and oligonucleotide target sequences used are listed in Tables 2 and 3. These sequences were adapted from a previous study to detect and identify MRSA strains. Molecular beacon probes were modified to contain a 5'-amino, an internal dT-Black Hole Quencher 2, and a 3'-biotin-TEG moiety (Glen Research). Molecular beacons were synthesized using standard automatic DNA chemistry on an ABI 394 DNA/RNA synthesizer (Applied Biosystems). In a post-synthesis step, a succinimidyl ester derivative of Texas-Red-X (Invitrogen) was conjugated to the 5' amino moiety. Before conjugation of the fluorophore, the oligonucleotide was purified by C-18 reverse phase High Pressure Liquid Chromatography (HPLC) to remove non-full-length oligonucleotides. The fluorophore was then conjugated by dissolving 1 mg of the fluorophore in dimethylformamide (Fisher Scientific) and adding this solution to 500 µL of 0.1 M NaHCO$_3$, at pH 8.2, which contained 5 nM 5'-amino labeled oligonucleotide, followed by overnight incubation at 37° C. After fluorophore conjugation, a second C-18 reverse phase HPLC purification was carried out to remove loose fluorophores and unconjugated oligonucleotides. A detailed protocol for the synthesis and purification of molecular beacon probes is available at www.molecular-beacons.org. Oligonucleotide targets were obtained from Integrated DNA Technologies.

TABLE 2

Sequences of molecular beacon probes (MB) and oligonucleotides used in this study.

| Name | Sequence (5' - 3') |
|---|---|
| mecA MB | Texas red-CGCGAT*TTCAATATGTATGCTTTGGTCTTTCTGC*ATCGCG-dT-BHQ2-TEG-biotin |
| spa MB | Texas red-CGCGAC*TTGTTGAGCTTCATCGTGTTGCGC*GTCGCG-dT-BHQ2-TEG-biotin |
| bac16S MB | Texas red-CGCTGG*CGAGCTGACGACAACCATGCACCACCAGCG-dT-BHQ2-TEG-biotin |
| mecA hairpin | Texas red-CGCGAT*TTCAATATGTATGCTTTGGTCTTTCTGC*ATCGCG-TEG-biotin |
| mecA target | CCAGGAAT*GCAGAAAGACCAAAGCATACATATT*GAAAATTTAAA |
| spa target | GCAAATGCT*GCGCAACACGATGAAGCTCAACAAAATGCTTTTTA |
| bac16S target | GAGTGACAGG*TGGTGCATGGTTGTCGTCAGCTCGTGTCGTGAG |

*a* The italic portions indicate the (molecular beacon)-target binding region

TABLE 3

Sequences of the 60, 98, and 200-nucleotide spa targets oligonucleotides and the PCR primers

| Name | Sequence (5' - 3') |
|---|---|
| spa 60-nucleotide target | CGTAACACCTGCTGCAAATGCTGCGCAACACGATGAAGCTCAACAAAATGCTTTTTATCA |
| spa 98-nucleotide target | CATTACTTATATCTGGTGGCGTAACACCTGCTGCAAATGCTGCGCAACACGATGAAGCTCAACAAAATGCTTTTTATCAAGTCTTAAATATGCCTAAC |
| spa 200-nucleotide target | TTATTCAATTCGTAAACTAGGTGTAGGTATTGCATCTGTAACTTTAGGTACATTACTTATATCTGGTGGCGTAACACCTGCTGCAAATGCTGCGCAACACGATGAAGCTCAACAAAATGCTTTTTATCAAGTCTTAAATATGCCTAACTTAAATGCTGATCAACGCAATGGTTTTATCCAAAGCCTTAAAGATGATCCAA |
| mecA forward primer | TGGTATGTGGAAGTTAGATTGG |
| mecA reverse primer | ATATGCTGTTCCTGTATTGGC |
| spa forward primer | CATTACTTATATCTGGTGGCG |
| spa reverse primer | GTTAGGCATATTTAAGACTTG |
| bac16S forward primer | TGGAGCATGTGGTTTAATTCGA |
| bac16S reverse primer | TGCGGGACTTAACCCAACA |

Characterization of Molecular Beacon Probes

The signal-to-background ratios of the molecular beacon probes in an aqueous solution were determined using a QuantaMaster spectrofluorometer (Photon Technology International). First, the fluorescence background ($I_{buffer}$) of 150 µL hybridization buffer (4 mM $MgCl_2$, 50 mM KCl, 10 mM Tris-HCl, pH 8.0) was monitored using an excitation wavelength of 583 nm and an emission wavelength of 603 nm. Then, 5 pmol of molecular beacon probe was added to the buffer solution, and the fluorescence background of the probe was monitored ($I_{MB}$). Finally, 100 pmol of oligonucleotide target was added, and the increase in fluorescence intensity was monitored until it reached a stable plateau ($I_{MB+t\ arg\ et}$). The hybridization buffer solution was kept at 50° C. throughout the assay.

Bacterial Strains and DNA Isolation

Genomic DNA isolated from *S. aureus* strains MRSA11512, a methicillin resistant strain, and MSSA21203, a methicillin sensitive strain (MSSA), were obtained from Dr. Barry Kreiswirth (Public Health Research Institute Tuberculosis Center). Briefly, single colonies of *S. aureus* were isolated on BBL CHROMagar *Staph aureus* (Becton-Dickinson) and grown overnight at 37° C. on Luria-Bertani (LB) agar plates. Genomic DNA was isolated using a Wizard® Genomic DNA Purification Kit (Promega), followed by treatment with 20 µg/mL lysostaphin (Sigma-Aldrich) for 30 min at 37° C. Genomic DNA was stored at 20° C.

Polymerase Chain Reactions

PCR primer pairs for the amplification of target regions from the mecA, spa, and 16s rRNA genes are listed in Table 3. The 16s rRNA gene sequence (bac16S) is common to all bacteria, the protein A gene (spa) is specific to *S. aureus*, and the mecA gene is unique to MRSA strains. In order to generate single-stranded amplification products containing the target sequence for the molecular beacon probes, an asymmetric PCR amplification was carried out. For each gene, 100 µL reaction volumes were prepared, containing 0.75 µM forward primer, 0.05 µM reverse primer, 5 units of Amplitaq Gold DNA polymerase (Applied Biosystems), 0.25 mM of each deoxyribonucleotide (Invitrogen), 4 mM $MgCl_2$, 50 mM KCl, 10 mM Tris-HCl, pH 8.0, and 5 ng total genomic bacterial DNA. The thermal cycling program includes an initial hold at 95° C. for 10 min to activate the DNA polymerase, followed by 40 cycles of 15 sec at 95° C., 30 sec at 55° C., and 30 sec at 72° C. Amplification products were stored at –20° C. and used without further purification as targets in the hybridization reactions. 20 µL of each amplification reaction was used in the hybridization experiments described below.

Fabrication of Biotinylated PEG Microgel Arrays

E-beam patterned PEG microgel surfaces were prepared using techniques similar to those described previously. 5 mm×7 mm silicon wafers (Ted Pella) were cleaned by exposure to piranha solution (3:1 $H_2SO_4/H_2O_2$) for 10 min at 120° C., rinsed three times in water, sonicated in water for 10 min and blown dry with nitrogen gas. A silanization procedure described by Papra et al. *Langmuir*, 2001, 17, 1457-1460. was used where the wafers were immersed in a 1 mM solution of 2-[methoxy(polyethyleneoxy)propyl]-trimethoxysilane (Gelest) dissolved in toluene. After overnight reaction, the wafers were washed once in toluene, twice in ethanol, twice in water, and then blown dry. Thin polymer films were spin-cast by dropping about 50 µL of a 2 wt % solution of biotinylated-PEG ($M_W$=5 kDa; Nanocs Inc.) in tetrahydrofuran at room temperature onto the silanized silicon wafer spinning at approximately 4000 rpm for 5 min. This procedure produced films with thicknesses of approximately 60 nm.

A Zeiss Auriga FIB-SEM CrossBeam Work Station equipped with a Nanometer Pattern Generation System (Nabity) was used to create the PEG microgel arrays. The incident electron energy was 2 keV, and the incident beam current was 160 pA. The working distance was 4.5 mm. The point electron dose used to create a single microgel, d, is given as d=DA/N, where D is the area dose with units of $\mu C/cm^2$ and N is the number of microgels patterned in an area A. The present experiments used a point dose of d=50 fC. Unirradiated or insufficiently cross-linked polymer was removed by immersing the silicon wafer in methanol for 10 min with 60 rpm shaking immediately after removal from the microscope. The wafer was then immersed twice in water for 5 min under 60 rpm gentle shaking and finally dried under blowing nitrogen Importantly, this process produces arrays of identical biotinylated PEG microgels with a controllable number of microgels, which can range from 1 microgel to over $10^7$ microgels, in an array. Most of the experiments here used arrays of 80 microgels patterned at an inter-gel distance of 1 µm within a circular area having a diameter of 10 µm.

Molecular Beacon Conjugation to PEG Microgels

Molecular beacons were conjugated to the surface-patterned biotinylated PEG microgels via biotin-streptavidin bonding. Biotinylated PEG microgel-patterned substrates were rehydrated for 1 hr at room temperature using a solution of 200 µg/mL streptavidin dissolved in 100 mM $Na_3PO_4$/150 mM NaCl (pH 7.4). The substrates were washed for 10 min using 100 mM $Na_3PO_4$/150 mM NaCl (pH 7.4) with 0.05% Tween-20 to remove excess streptavidin. The substrates were then washed twice in Tween-free buffer, once in water, and dried by centrifugation (500 g, 2 min) Biotinylated molecular beacons were dissolved in 10 mM $Na_3PO_4$/15 mM NaCl (pH 7.4) to a concentration of $10^{-6}$ M, and streptavidin-conjugated biotinylated PEG microgel substrates were exposed to this solution overnight at room temperature in a humid atmosphere. The substrates were then rinsed three times in 10 mM $Na_3PO_4$/15 mM NaCl (pH 7.0) buffer, washed in water, and dried by centrifugation.

Hybridization Experiments

Hybridization experiments were carried out by rehydrating the microgel-tethered molecular beacon arrays with 20 µL of hybridization buffer (4 mM $MgCl_2$, 50 mM KCl, 10 mM Tris-HCl, pH 8.0) containing controlled concentrations (typically 1 µM) of oligonucleotide targets followed by incubation at 50° C. for 1 hr in a humid atmosphere. The surfaces were then washed by a sequence of preheated (50° C.) washing buffers. The three washing buffers—designated A, B, and C—were made by mixing 15, 10, or 5 mL, respectively, of 1 M saline-sodium phosphate-EDTA (SSPE) solution with 35, 40, or 45 mL, respectively, of deionized water. Triton X-100 was dissolved in each to a final concentration of 0.01%. After washing in each of these buffers, the surfaces were allowed to cool to room temperature.

Fluorescence images, before and after hybridization, were taken at room temperature using a Nikon E1000 Fluorescence Microscope with a SensiCam high-sensitivity CCD Camera (Cooke). Imaging was carried out using a Nikon Plan Apo VC 60×(NA=1.2) water-immersion objective lens. A typical exposure time was 2 sec.

the Number of Micro Gel Binding Sites

The average number of streptavidins conjugated to one single microgel was estimated by measuring the fluorescence intensity of single Texas-red labeled streptavidins released from a known number of microgels. First, Texas-red labeled streptavidins were conjugated to a surface covered by a known number of biotinylated-PEG microgels. Excess protein was washed off by a treatment with 0.05% Tween-20 solution (described above). 500 μL 95% formamide solution, containing 10 mM EDTA, (pH 8.2) was added to the surface and incubated for 1 hr at 65° C. to release the Texas-red labeled streptavidin molecules. The total fluorescence intensity of the buffer was then measured on a spectrofluorometer. The average number of streptavidin molecules per microgel was determined by fitting the data in a standard curve, calibrated with a set of serial dilutions of Texas-red-streptavidin dissolved in 95% formamide solution, containing 10 mM EDTA, (pH 8.2). Based on fluorescence images of the patterned surface before and after the formamide procedure, the efficiency of streptavidin release from the surface was determined to be over 95%.

To estimate the average number of molecular beacon probes on each microgel, the fluorescence intensity of biotinylated Texas-red labeled oligonucleotides (mecA hairpin, see Table 2) released from a known number of microgels was measured. The procedure described above for releasing the streptavidin was repeated, with the exception that the excess oligonucleotide was washed off with a 10 mM $Na_3PO_4$/15 mM NaCl (pH 7.0) solution, and a standard curve was constructed with a serial dilution of biotinylated Texas-red labeled oligonucleotides. Again, based on fluorescence images of the patterned surface before and after the formamide procedure, the efficiency of the molecular beacon release from the surface was determined to be over 90%.

Monte Carlo Simulation

The interaction of incident electrons with thin biotinylated PEG films was simulated using Monte Carlo methods. What was modeled was the case of a film 65 nm thick with a density of 1.05 $g/cm^3$ covering a semi-infinite Si substrate impacted at a single point, (0, 0, 0), by as many as 320,000 electrons (about 50 fC), each with an energy of 2 keV. Single-electron trajectories were followed with decisions of scattering type—elastic or inelastic—scattering angle, and energy change due to electron-nuclei interactions made using a random-number generator weighted by a screened Rutherford elastic cross section. Energy deposition was accounted for using a modified expression for the Bethe stopping power:

$$S = \frac{dE}{dx} = \frac{-78,500Z}{AE} \ln\left[\frac{1.166(E + KJ)}{J}\right] \quad (3)$$

where $K=0.734Z^{0.037}$ and S, Z, A, E, and J are the stopping power, atomic number, atomic weight, instantaneous energy and mean ionization potential, respectively. Individual electron trajectories were followed until the electron energy fell below a threshold of 50 eV or until an electron reached the top surface of the specimen, (x, y, z=0), where it escaped into the surrounding vacuum. The coordinates of each electron trajectory were recorded in one of three different arrays: (1) as a primary electron in the PEG film; (2) as a primary electron in the Si; and (3) as an electron backscattered from the Si substrate into the PEG film. Energy deposition in the Si substrate was ignored, since the semi-infinite Si is a good heat sink Energy deposition in the PEG film was accumulated in 1 $nm^3$ voxels.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. A device for simultaneously detecting multiple biological targets comprising:
   (i) a plurality of quenched probes that comprise individual quenched probes comprising labeled single-hairpin molecules that undergo a conformational change when individual quenched probes are bound to individual biological targets, wherein said conformational change leads to a detectable signal;
   (ii) a plurality of structures that comprise individual structures comprising a plurality of linking moieties, and further comprising a hydrated hydrophilic medium selected from the group consisting of aqueous gels, aqueous microgels, and aqueous gel coatings,
   wherein the hydrated hydrophilic medium is tethered to the plurality of quenched probes through the plurality of linking moieties,
   wherein the hydrated hydrophilic medium has a gradual transition region comprising a progressively reduced crosslink density from a center of the hydrated hydrophilic medium to a surface of the hydrated hydrophilic medium; and
   (iii) a substrate, wherein the plurality of structures are arranged in a spatially separated array on the substrate.

2. The device according to claim 1 wherein the gradual transition region has a thickness at least equal to the combined lengths of the individual quenched probes crosslinked to the individual linking moieties.

3. The device of claim 2 wherein the plurality of quenched probes are hairpin oligonucleotides labeled with a fluorophore and a non-fluorescent quencher.

4. The device of claim 3 wherein the multiple biological targets are nucleic acids or peptides.

5. The device of claim 4 wherein the hydrated hydrophilic medium is a surface-patterned microgel.

6. The device according to claim 5 wherein the plurality of linking moieties comprise streptavidin-biotin moieties.

7. The device according to claim 5 wherein the surface-patterned microgel is poly(ethylene glycol).

8. The device according to claim 2 wherein the hydrated hydrophilic medium is an electron-beam surface patterned microgel.

9. The device according to claim 3 wherein the hairpin oligonucleotides include non-natural nucleotides, nucleotide analogs, or non-natural inter-nucleotide linkages.

10. The device according to claim 1 wherein the hydrated hydrophilic medium is biotinylated, e-beam patterned poly (ethylene glycol) microgel.

11. The device according to claim 1, wherein a majority of the plurality of quenched probes are separated from the substrate by a distance of at least as large as the combined length of the individual quenched probes crosslinked to the individual linking moieties.

12. The device of claim 1, wherein the plurality of quenched probes has a signal-to-background (SBR) ratio of at least 5.

13. The device of claim 1, wherein the plurality of quenched probes has a signal-to-background (SBR) ratio of at least 10.

14. The device of claim 1, wherein the plurality of quenched probes has a signal-to-background (SBR) ratio of at least 20.

15. The device of claim 1, wherein the plurality of quenched probes has a signal-to-background (SBR) ratio of at least 30.

16. The device of claim 1, wherein the plurality of quenched probes has a signal-to-background (SBR) ratio greater than 30.

17. A method for simultaneously detecting the presence of one or more targets in a biological sample comprising:
   (a) providing a device of claim 1
   (b) contacting the device with the biological sample for a period of time under conditions permitting binding between the one or more targets and the corresponding plurality of quenched probes; and
   (c) determining the presence of the binding between the one or more targets and the corresponding plurality of quenched probes thereby detecting the presence of the one or more targets.

* * * * *

SEQUENCE LISTING

```
<160> NUMBER OF SEQ ID NOS: 16

<210> SEQ ID NO 1
<211> LENGTH: 40
<212> TYPE: DNA
<213> ORGANISM: Artificial
<220> FEATURE:
<223> OTHER INFORMATION: Synthetic probe

<400> SEQUENCE: 1
cgcgatttca atatgtatgc tttggtcttt ctgcatcgcg                          40

<210> SEQ ID NO 2
<211> LENGTH: 36
<212> TYPE: DNA
<213> ORGANISM: Artificial
<220> FEATURE:
<223> OTHER INFORMATION: Synthetic probe

<400> SEQUENCE: 2
cgcgacttgt tgagcttcat cgtgttgcgc gtcgcg                              36

<210> SEQ ID NO 3
<211> LENGTH: 36
<212> TYPE: DNA
<213> ORGANISM: Artificial
<220> FEATURE:
<223> OTHER INFORMATION: Synthetic probe

<400> SEQUENCE: 3
```

```
cgctggcgag ctgacgacaa ccatgcacca ccagcg                         36
```

<210> SEQ ID NO 4
<211> LENGTH: 40
<212> TYPE: DNA
<213> ORGANISM: Artificial
<220> FEATURE:
<223> OTHER INFORMATION: Synthetic
<400> SEQUENCE: 4

```
cgcgatttca atatgtatgc tttggtcttt ctgcatcgcg                     40
```

<210> SEQ ID NO 5
<211> LENGTH: 44
<212> TYPE: DNA
<213> ORGANISM: Artificial
<220> FEATURE:
<223> OTHER INFORMATION: Synthetic
<400> SEQUENCE: 5

```
ccaggaatgc agaaagacca aagcatacat attgaaaatt taaa                44
```

<210> SEQ ID NO 6
<211> LENGTH: 44
<212> TYPE: DNA
<213> ORGANISM: Artificial
<220> FEATURE:
<223> OTHER INFORMATION: Synthetic
<400> SEQUENCE: 6

```
gcaaatgctg cgcaacacga tgaagctcaa caaaatgctt ttta                44
```

<210> SEQ ID NO 7
<211> LENGTH: 43
<212> TYPE: DNA
<213> ORGANISM: Artificial
<220> FEATURE:
<223> OTHER INFORMATION: Synthetic
<400> SEQUENCE: 7

```
gagtgacagg tggtgcatgg ttgtcgtcag ctcgtgtcgt gag                 43
```

<210> SEQ ID NO 8
<211> LENGTH: 60
<212> TYPE: DNA
<213> ORGANISM: Artificial
<220> FEATURE:
<223> OTHER INFORMATION: Synthetic
<400> SEQUENCE: 8

```
cgtaacacct gctgcaaatg ctgcgcaaca cgatgaagct caacaaaatg cttttatca 60
```

<210> SEQ ID NO 9
<211> LENGTH: 98
<212> TYPE: DNA
<213> ORGANISM: Artificial
<220> FEATURE:
<223> OTHER INFORMATION: Synthetic
<400> SEQUENCE: 9

```
cattacttat atctggtggc gtaacacctg ctgcaaatgc tgcgcaacac gatgaagctc 60
aacaaaatgc ttttatcaa gtcttaaata tgcctaac                        98
```

<210> SEQ ID NO 10

```
<211> LENGTH: 200
<212> TYPE: DNA
<213> ORGANISM: Artificial
<220> FEATURE:
<223> OTHER INFORMATION: Synthetic

<400> SEQUENCE: 10
ttattcaatt cgtaaactag gtgtaggtat tgcatctgta actttaggta cattacttat      60
atctggtggc gtaacacctg ctgcaaatgc tgcgcaacac gatgaagctc aacaaaatgc     120
tttttatcaa gtcttaaata tgcctaactt aaatgctgat caacgcaatg gttttatcca     180
aagccttaaa gatgatccaa                                                 200

<210> SEQ ID NO 11
<211> LENGTH: 22
<212> TYPE: DNA
<213> ORGANISM: Artificial
<220> FEATURE:
<223> OTHER INFORMATION: Synthetic

<400> SEQUENCE: 11
tggtatgtgg aagttagatt gg                                               22

<210> SEQ ID NO 12
<211> LENGTH: 21
<212> TYPE: DNA
<213> ORGANISM: Artificial
<220> FEATURE:
<223> OTHER INFORMATION: Synthetic

<400> SEQUENCE: 12
atatgctgtt cctgtattgg c                                                21

<210> SEQ ID NO 13
<211> LENGTH: 21
<212> TYPE: DNA
<213> ORGANISM: Artificial
<220> FEATURE:
<223> OTHER INFORMATION: Synthetic

<400> SEQUENCE: 13
cattacttat atctggtggc g                                                21

<210> SEQ ID NO 14
<211> LENGTH: 21
<212> TYPE: DNA
<213> ORGANISM: Artificial
<220> FEATURE:
<223> OTHER INFORMATION: Synthetic

<400> SEQUENCE: 14
gttaggcata tttaagactt g                                                21

<210> SEQ ID NO 15
<211> LENGTH: 22
<212> TYPE: DNA
<213> ORGANISM: Artificial
<220> FEATURE:
<223> OTHER INFORMATION: Synthetic

<400> SEQUENCE: 15
tggagcatgt ggtttaattc ga                                               22

<210> SEQ ID NO 16
<211> LENGTH: 19
```

```
<212> TYPE: DNA
<213> ORGANISM: Artificial
<220> FEATURE:
<223> OTHER INFORMATION: Synthetic

<400> SEQUENCE: 16
tgcgggactt aacccaaca                                            19
```